(12) United States Patent
Mootien et al.

(10) Patent No.: US 10,064,670 B2
(45) Date of Patent: Sep. 4, 2018

(54) SACRAL FIXATION SYSTEM

(71) Applicant: DePuy Synthes Products, Inc., Raynham, MA (US)

(72) Inventors: Azagen Mootien, Rantzwiller (FR); Alfred Niederberger, Grenches (CH); Johann Fierlbeck, Salzburg (AT); Martin Altmann, Oberdorf (CH); Martin Kaufmann, Zuchwil (CH)

(73) Assignee: Depuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/708,439

(22) Filed: May 11, 2015

(65) Prior Publication Data
US 2015/0320451 A1 Nov. 12, 2015

Related U.S. Application Data

(60) Provisional application No. 61/991,837, filed on May 12, 2014.

(51) Int. Cl.
*A61B 17/70* (2006.01)
*A61B 17/86* (2006.01)
(Continued)

(52) U.S. Cl.
CPC ...... *A61B 17/8685* (2013.01); *A61B 17/1671* (2013.01); *A61B 17/1757* (2013.01);
(Continued)

(58) Field of Classification Search
CPC .......... A61B 17/7055; A61B 17/7062–17/707; A61B 17/84–17/86; A61F 2/4611
See application file for complete search history.

(56) References Cited

U.S. PATENT DOCUMENTS 2,143,922 A   1/1939  Longfellow
2,489,870 A * 11/1949  Dzus ............... A61B 17/683
                                                411/339
(Continued)

FOREIGN PATENT DOCUMENTS

CN      202843773      4/2013
DE  202007017159 U1    6/2008
(Continued)

OTHER PUBLICATIONS

International Search Report issued in PCT/US2015/030087 dated Oct. 27, 2015, 8 pages.
(Continued)

*Primary Examiner* — Eduardo C Robert
*Assistant Examiner* — Michelle C Eckman
(74) *Attorney, Agent, or Firm* — Baker & Hostetler LLP

(57) ABSTRACT

A sacral fixation implant can include at least one implant segment, a guide wire, and at least one locking member that is configured to fix the implant segment to the guide wire. The implant segment can be configured to be secured to an ilium bone, and the guide wire can be configured to be secured to the sacrum. The implant can include first and second implant segments that are configured to be secured to opposed ilium bones, such that a first locking member is configured to fix the first implant segment to the guide wire, and a second locking member is configured to fix the second implant segment to the guide wire.

20 Claims, 6 Drawing Sheets

(51) Int. Cl.
*A61B 17/84* (2006.01)
*A61B 17/16* (2006.01)
*A61B 17/17* (2006.01)
*A61B 17/68* (2006.01)
*A61B 90/00* (2016.01)

(52) U.S. Cl.
CPC ........ *A61B 17/683* (2013.01); *A61B 17/7055* (2013.01); *A61B 17/7091* (2013.01); *A61B 17/844* (2013.01); *A61B 2090/3966* (2016.02)

(56) References Cited

U.S. PATENT DOCUMENTS

| | | | |
|---|---|---|---|
| 2,511,051 A * | 6/1950 | Dzus | A61B 17/683 411/338 |
| 2,586,556 A * | 2/1952 | Mullikin | B42F 13/02 402/57 |
| 4,016,874 A * | 4/1977 | Maffei | A61B 17/72 606/62 |
| 4,047,523 A | 9/1977 | Hall | |
| 4,409,974 A | 10/1983 | Freedland | |
| 4,530,114 A | 7/1985 | Tepic | |
| 4,569,338 A | 2/1986 | Edwards | |
| 4,590,928 A | 5/1986 | Hunt et al. | |
| 4,612,918 A * | 9/1986 | Slocum | A61B 17/7055 606/279 |
| 4,640,271 A * | 2/1987 | Lower | A61B 17/8685 606/105 |
| 4,858,601 A * | 8/1989 | Glisson | A61B 17/8685 411/389 |
| 4,930,499 A | 6/1990 | Rowe | |
| RE33,348 E * | 9/1990 | Lower | A61B 17/8685 606/304 |
| 5,000,165 A | 3/1991 | Watanabe | |
| 5,108,397 A | 4/1992 | White | |
| 5,127,912 A | 7/1992 | Ray et al. | |
| 5,129,904 A | 7/1992 | Illi | |
| 5,152,794 A | 10/1992 | Davidson | |
| 5,242,444 A * | 9/1993 | MacMillan | A61B 17/1757 606/60 |
| 5,300,073 A | 4/1994 | Ray et al. | |
| 5,306,275 A | 4/1994 | Bryan | |
| 5,382,257 A | 1/1995 | Lewis et al. | |
| 5,458,599 A | 10/1995 | Adobbati | |
| 5,490,855 A * | 2/1996 | Bouraly | A61B 17/15 606/82 |
| 5,515,562 A | 5/1996 | Miller et al. | |
| 5,620,445 A | 4/1997 | Brosnahan et al. | |
| 5,797,915 A | 8/1998 | Rierson III et al. | |
| 5,800,544 A | 9/1998 | Demopulos et al. | |
| 5,827,285 A * | 10/1998 | Bramlet | A61B 17/68 411/166 |
| 5,885,294 A | 3/1999 | Pedlick et al. | |
| 5,899,901 A | 5/1999 | Middleton | |
| 5,919,194 A | 7/1999 | Anderson | |
| 5,989,252 A | 11/1999 | Fumex | |
| 5,997,538 A * | 12/1999 | Asnis | A61B 17/8625 606/301 |
| 6,004,327 A * | 12/1999 | Asnis | A61B 17/8869 606/104 |
| 6,010,505 A | 1/2000 | Asche et al. | |
| 6,041,485 A | 3/2000 | Pedlick et al. | |
| 6,080,192 A | 6/2000 | Demopulos et al. | |
| 6,106,556 A | 6/2000 | Demopulos et al. | |
| 6,126,660 A | 10/2000 | Dietz | |
| 6,168,631 B1 * | 1/2001 | Maxwell | A61B 17/562 623/17.11 |
| 6,197,028 B1 | 3/2001 | Ray et al. | |
| 6,197,065 B1 | 3/2001 | Martin et al. | |
| 6,203,543 B1 * | 3/2001 | Glossop | A61B 17/86 606/246 |
| 6,214,004 B1 | 4/2001 | Coker | |
| 6,302,887 B1 * | 10/2001 | Spranza | A61B 17/683 411/338 |
| 6,319,254 B1 * | 11/2001 | Giet | A61B 17/863 606/104 |
| 6,348,053 B1 | 2/2002 | Cachia | |
| 6,368,326 B1 | 4/2002 | Dakin et al. | |
| 6,508,841 B2 | 1/2003 | Martin et al. | |
| 6,520,990 B1 | 2/2003 | Ray | |
| 6,544,267 B1 | 4/2003 | Cole et al. | |
| 6,558,387 B2 | 5/2003 | Errico et al. | |
| 6,565,568 B1 | 5/2003 | Rogozinski | |
| 6,602,214 B2 | 8/2003 | Heinz et al. | |
| 6,613,059 B2 | 9/2003 | Schaller et al. | |
| 6,626,916 B1 | 9/2003 | Yeung et al. | |
| 6,648,890 B2 | 11/2003 | Culbert et al. | |
| 6,648,903 B1 | 11/2003 | Pierson, III | |
| 6,712,855 B2 | 3/2004 | Martin et al. | |
| 6,730,092 B2 | 5/2004 | Songer | |
| 6,761,722 B2 | 7/2004 | Cole et al. | |
| 7,037,308 B2 | 5/2006 | Medoff | |
| 7,153,305 B2 | 12/2006 | Johnson et al. | |
| 7,326,222 B2 | 2/2008 | Dreyfuss et al. | |
| 7,410,489 B2 | 8/2008 | Dakin et al. | |
| 7,651,528 B2 | 1/2010 | Montgomery et al. | |
| 7,670,383 B1 * | 3/2010 | Brown | A61F 2/28 623/22.22 |
| 7,704,252 B2 | 4/2010 | Albertson et al. | |
| 7,722,643 B2 | 5/2010 | Schaller et al. | |
| 7,749,255 B2 | 7/2010 | Johnson et al. | |
| 7,771,426 B2 | 8/2010 | Burch et al. | |
| 7,780,707 B2 | 8/2010 | Johnson et al. | |
| 7,789,895 B2 | 9/2010 | Heinz | |
| 7,799,057 B2 | 9/2010 | Hudgins et al. | |
| 7,892,255 B2 | 2/2011 | Schaller et al. | |
| 7,938,832 B2 | 5/2011 | Culbert et al. | |
| 7,947,064 B2 | 5/2011 | Bergeron et al. | |
| 8,790,406 B1 * | 7/2014 | Smith | A61F 2/4455 600/202 |
| 9,358,057 B1 * | 6/2016 | Whipple | A61B 17/7055 |
| 9,788,862 B2 * | 10/2017 | Mootien | A61B 17/683 |
| 2001/0000186 A1 | 4/2001 | Bramlet | |
| 2002/0087161 A1 | 7/2002 | Randall et al. | |
| 2002/0198527 A1 * | 12/2002 | Muckter | A61B 17/8685 606/316 |
| 2003/0078584 A1 * | 4/2003 | Tipirneni | A61B 17/68 606/916 |
| 2003/0236555 A1 * | 12/2003 | Thornes | A61B 17/0401 606/232 |
| 2004/0097941 A1 * | 5/2004 | Weiner | A61B 17/685 606/312 |
| 2004/0167519 A1 * | 8/2004 | Weiner | A61B 17/8665 606/60 |
| 2004/0172031 A1 * | 9/2004 | Rubecamp | A61B 17/8685 606/309 |
| 2004/0260297 A1 | 12/2004 | Padget et al. | |
| 2005/0143735 A1 * | 6/2005 | Kyle | A61B 17/8685 606/60 |
| 2005/0222575 A1 * | 10/2005 | Ciccone | A61B 17/1615 606/104 |
| 2005/0234459 A1 * | 10/2005 | Falahee | A61B 17/1757 606/323 |
| 2006/0161261 A1 * | 7/2006 | Brown | A61F 2/28 623/22.22 |
| 2006/0264954 A1 * | 11/2006 | Sweeney, II | A61B 17/8685 606/312 |
| 2007/0014649 A1 * | 1/2007 | James | A61B 17/863 411/81 |
| 2007/0162026 A1 * | 7/2007 | Tipirneni | A61B 17/68 606/916 |
| 2007/0213732 A1 * | 9/2007 | Khanna | A61B 17/8685 606/86 A |
| 2007/0260248 A1 * | 11/2007 | Tipirneni | A61B 17/68 606/65 |
| 2008/0140082 A1 * | 6/2008 | Erdem | A61B 17/8805 606/92 |
| 2008/0147126 A1 * | 6/2008 | Tipirneni | A61B 17/68 606/300 |
| 2008/0147127 A1 * | 6/2008 | Tipirneni | A61B 17/742 606/301 |

(56) References Cited

U.S. PATENT DOCUMENTS

| | | | |
|---|---|---|---|
| 2008/0177306 A1 | 7/2008 | Lamborne et al. | |
| 2008/0243191 A1* | 10/2008 | Tipirneni | A61B 17/742 606/280 |
| 2009/0099610 A1* | 4/2009 | Johnson | A61B 17/844 606/86 R |
| 2009/0131936 A1* | 5/2009 | Tipirneni | A61B 17/683 606/64 |
| 2009/0131991 A1* | 5/2009 | Tipirneni | A61B 17/683 606/301 |
| 2009/0198288 A1* | 8/2009 | Hoof | A61B 17/8615 606/301 |
| 2009/0228008 A1* | 9/2009 | Justin | A61B 5/107 606/62 |
| 2009/0228049 A1 | 9/2009 | Park | |
| 2009/0254129 A1* | 10/2009 | Tipirneni | A61B 17/742 606/309 |
| 2009/0259261 A1* | 10/2009 | Reiley | A61B 17/8897 606/329 |
| 2009/0306718 A1* | 12/2009 | Tipirneni | A61B 17/683 606/263 |
| 2009/0312798 A1* | 12/2009 | Varela | A61B 17/7064 606/247 |
| 2010/0036440 A1 | 2/2010 | Morris et al. | |
| 2010/0168802 A1* | 7/2010 | Pathak | A61B 17/60 606/305 |
| 2010/0198267 A1* | 8/2010 | Vaidya | A61B 17/68 606/286 |
| 2010/0204700 A1* | 8/2010 | Falahee | A61B 17/7064 606/80 |
| 2010/0217329 A1* | 8/2010 | Brown | A61B 17/742 606/301 |
| 2010/0312292 A1* | 12/2010 | Tipirneni | A61B 17/92 606/86 R |
| 2011/0034925 A1* | 2/2011 | Tipirneni | A61B 17/683 606/62 |
| 2011/0071576 A1* | 3/2011 | Hadi | A61B 17/683 606/301 |
| 2011/0071578 A1* | 3/2011 | Colesanti | A61B 17/064 606/305 |
| 2011/0087296 A1* | 4/2011 | Reiley | A61B 17/68 606/303 |
| 2011/0137356 A1* | 6/2011 | Kollmer | A61B 17/1767 606/324 |
| 2011/0184519 A1* | 7/2011 | Trieu | A61B 17/7076 623/17.11 |
| 2011/0238181 A1* | 9/2011 | Trieu | A61B 17/1735 623/17.11 |
| 2011/0264229 A1* | 10/2011 | Donner | A61F 2/30988 623/18.11 |
| 2011/0295252 A1* | 12/2011 | Tipirneni | A61B 17/685 606/62 |
| 2012/0203352 A1* | 8/2012 | Perez, III | A61F 2/3601 623/23.11 |
| 2012/0239095 A1* | 9/2012 | Barrall | A61B 17/1655 606/301 |
| 2012/0245704 A1* | 9/2012 | Childs | A61B 17/7064 623/23.52 |
| 2013/0018427 A1* | 1/2013 | Pham | A61B 17/7055 606/301 |
| 2013/0030456 A1* | 1/2013 | Assell | A61B 17/84 606/170 |
| 2013/0035727 A1* | 2/2013 | Datta | A61B 17/7055 606/279 |
| 2013/0079776 A1* | 3/2013 | Zwirkoski | A61B 17/68 606/62 |
| 2013/0158609 A1* | 6/2013 | Mikhail | A61B 17/683 606/305 |
| 2013/0190772 A1* | 7/2013 | Doerr | A61B 17/86 606/104 |
| 2013/0226239 A1* | 8/2013 | Altarac | A61B 17/7064 606/247 |
| 2013/0267836 A1* | 10/2013 | Mauldin | A61B 6/12 600/424 |
| 2013/0296953 A1* | 11/2013 | Mauldin | A61B 17/84 606/328 |
| 2014/0031935 A1* | 1/2014 | Donner | A61F 2/4455 623/17.11 |
| 2014/0046380 A1* | 2/2014 | Asfora | A61B 17/1615 606/304 |
| 2014/0135850 A1* | 5/2014 | Parent | A61B 17/68 606/304 |
| 2014/0135927 A1* | 5/2014 | Pavlov | A61B 17/7055 623/17.11 |
| 2014/0142700 A1* | 5/2014 | Donner | A61F 2/44 623/17.11 |
| 2014/0228898 A1* | 8/2014 | Gordon | A61B 17/84 606/328 |
| 2014/0236242 A1* | 8/2014 | Robinson | A61B 17/8605 606/279 |
| 2014/0257408 A1* | 9/2014 | Trieu | A61B 17/8875 606/301 |
| 2014/0257412 A1* | 9/2014 | Patty | A61B 17/8615 606/308 |
| 2014/0276827 A1* | 9/2014 | Roman | A61B 17/7291 606/64 |
| 2014/0276851 A1* | 9/2014 | Schneider | A61B 17/846 606/84 |
| 2014/0277139 A1* | 9/2014 | Vrionis | A61B 17/70 606/246 |
| 2014/0277460 A1* | 9/2014 | Schifano | A61F 2/4611 623/17.11 |
| 2014/0277463 A1* | 9/2014 | Yerby | A61F 2/32 623/17.11 |
| 2014/0277558 A1* | 9/2014 | Kurtz | A61B 17/0401 623/22.36 |
| 2014/0288601 A1* | 9/2014 | Baynham | A61B 17/7064 606/247 |
| 2014/0288605 A1* | 9/2014 | Mesiwala | A61B 17/7055 606/279 |
| 2015/0048057 A1* | 2/2015 | Wada | B23K 9/167 219/75 |
| 2015/0094765 A1* | 4/2015 | Donner | A61B 17/1735 606/246 |
| 2015/0105828 A1* | 4/2015 | Reckling | A61B 17/1659 606/279 |
| 2015/0150615 A1* | 6/2015 | Anapliotis | A61B 17/8685 606/305 |
| 2015/0157425 A1* | 6/2015 | Bar Shalom | A61C 8/0025 433/174 |
| 2015/0201985 A1* | 7/2015 | Rampersaud | A61B 17/8875 606/86 A |
| 2015/0216565 A1* | 8/2015 | Paley | A61B 17/68 606/328 |
| 2015/0257800 A1* | 9/2015 | Harshman | A61B 17/7208 606/62 |
| 2015/0320450 A1* | 11/2015 | Mootien | A61B 17/1703 606/246 |
| 2015/0320451 A1* | 11/2015 | Mootien | A61B 17/8685 606/246 |
| 2015/0320464 A1* | 11/2015 | Schmidt | A61B 17/863 606/304 |
| 2015/0342656 A1* | 12/2015 | Bertollo | A61B 17/8685 606/304 |
| 2015/0342753 A1* | 12/2015 | Donner | A61B 17/1757 623/18.11 |
| 2016/0015483 A1* | 1/2016 | Kumar | A61C 8/0012 606/301 |
| 2016/0030096 A1* | 2/2016 | Roman | A61F 2/4225 606/62 |
| 2016/0038186 A1* | 2/2016 | Herzog | A61B 17/683 606/304 |

(56) References Cited

U.S. PATENT DOCUMENTS

| | | | |
|---|---|---|---|
| 2016/0040708 A1* | 2/2016 | Limatoc | F16B 39/284 411/306 |
| 2016/0120661 A1* | 5/2016 | Schell | A61F 2/4601 623/17.11 |
| 2016/0143671 A1* | 5/2016 | Jimenez | A61B 17/7055 606/304 |
| 2016/0157897 A1* | 6/2016 | Vaidya | A61B 17/8066 606/279 |

FOREIGN PATENT DOCUMENTS

| | | |
|---|---|---|
| EP | 0085493 | 8/1983 |
| EP | 0260222 | 3/1988 |
| FR | 1046555 | 12/1953 |
| WO | WO 2010/019384 | 2/2010 |

OTHER PUBLICATIONS

Acharya NK, Bijukachhe B, Kumar RJ, Menon VK. Ilio-lumbar fixation—the Amrita technique. J Spinal Disord Tech. Oct. 2008;21(7):493-9.

Ebraheim NA, Coombs R, Jackson WT, Rusin JJ. Percutaneous computed tomography-guided stabilization of posterior pelvic fractures. Clin Orthop Relat Res. Oct. 1994;(307):222-8.

Ebraheim NA, Padanilam TG, Waldrop JT, Yeasting RA. Anatomic consideration in the anterior approach to the sacro-iliac joint. Spine (Phila PA 1976). Mar. 15, 1994;19(6):721-5.

Fuchs T, Rottbeck U, Hofbauer V, Raschke M, Stange R. [Pelvic ring fractures in the elderly. Underestimated osteoporotic fracture]. Unfallchirurg. Aug. 2011;114(8):663-70.

Gänsslen A, Krettek C. Retrograde transpubic screw fixation of transpubic instabilities. Oper Orthop Traumatol. Oct. 2006;18(4):330-40.

Gänsslen A, Hufner T, Krettek C. Percutaneous iliosacral screw fixation of unstable pelvic injuries by conventional fluoroscopy. Oper Orthop Traumatol. Sep. 2006;18(3):225-44.

Gardner MJ, Routt ML Jr. Transiliac-transsacral screws for posterior pelvic stabilization. J Orthop Trauma. Jun. 2011;25(6):378-84.

Iguchi T, Ogawa K, Doi T, Miyasho K, Munetomo K, Hiraki T, Ozaki T, Kanazawa S. Computed tomography fluoroscopy-guided placement of iliosacral screws in patients with unstable posterior pelvic fractures. Skeletal Radio. Jul. 2010;39(7):701-5.

Sciulli RL, Daffner RH, Altman DT, Altman GT, Sewecke JJ. CT-guided iliosacral screw placement: technique and clinical experience. AJR Am J Roentgenol. Feb. 2007;188(2).

Schildhauer TA, Ledoux WR, Chapman JR, Henley MB, Tencer AF, Routt ML Jr. Triangular osteosynthesis and iliosacral screw fixation for unstable sacral fractures: a cadaveric and biomechanical evaluation under cyclic loads. J Orthop Trauma. Jan. 2003;17(1):22-31.

Sciubba DM, Petteys RJ, Dekutoski MB, Fisher CG, Fehlings MG, Ondra SL, Rhines LD, Gokaslan ZL. Diagnosis and management of metastatic spine disease. A review. J Neurosurg Spine. Jul. 2010;13(1):94-108.

Pohlemann T, Gänsslen A, Tscherne H. [Fracture of the sacrum]. Unfallchirurg. Sep. 2000;103(9):769-86.

Pohlemann T, Richter M, Otte D, Gänsslen A, Bartram H, Tscherne H. [Mechanism of pelvic girdle injuries in street traffic. Medical-technical accident analysis]. Unfallchirurg. Apr. 2000;103(4):267-74.

Suzuki T, Hak DJ, Ziran BH, Adams SA, Stahel PF, Morgan SJ, Smith WR. Outcome and complications of posterior transiliac plating for vertically unstable sacral fractures. Injury. Apr. 2009;40(4):405-9.

Anselmetti GC, Bonaldi G, Carpeggiani P, Manfrè L, Masala S, Muto M. Vertebral augmentation: 7 years experience. Acta Neurochir Suppl. 2011;108:147-61. doi:10.1007/978-3-211-99370-5_23. Review. PubMed PMID: 21107952.

Butler CL, Given CA 2nd, Michel SJ, Tibbs PA. Percutaneous sacroplasty for the treatment of sacral insufficiency fractures. AJR Am J Roentgenol. Jun. 2005;184(6):1956-9. PubMed PMID: 15908561.

Frey ME, Depalma MJ, Cifu DX, Bhagia SM, Came W, Daitch JS. Percutaneous sacroplasty for osteoporotic sacral insufficiency fractures: a prospective, multicenter, observational pilot study. Spine J. Mar.-Apr. 2008;8(2):367-73. Epub Jul. 20, 2007.

Garant M. Sacroplasty: a new treatment for sacral insufficiency fracture. J Vasc Intery Radiol. Dec. 2002;13(12):1265-7.

Heron J, Connell DA, James SL. CT-guided sacroplasty for the treatment of sacral insufficiency fractures. Clin Radiol. Nov. 2007;62(11):1094-100; discussion 1101-3. Epub Aug. 13, 2007.

Ortiz AO, Brook AL. Sacroplasty. Tech Vasc Intery Radiol. Mar. 2009;12(1):51-63.

Pommersheim W, Huang-Hellinger F, Baker M, Morris P. Sacroplasty: a treatment for sacral insufficiency fractures. AJNR Am J Neuroradiol. May 2003;24(5):1003-7.

Zaman FM, Frey M, Slipman CW. Sacral stress fractures. Curr Sports Med Rep. Feb. 5, 2006,(1):37-43.

Sagi HC. Technical aspects and recommended treatment algorithms in triangular osteosynthesis and spinopelvic fixation for vertical shear transforaminal sacral fractures. J Orthop Trauma. May-Jun. 2009;23(5):354-60.

Sagi HC, Militano U, Caron T, Lindvall E. A comprehensive analysis with minimum 1-year follow-up of vertically unstable transforaminal sacral fractures treated with triangular osteosynthesis. J Orthop Trauma. May-Jun. 2009;23(5):313-9; discussion 319-21.

* cited by examiner

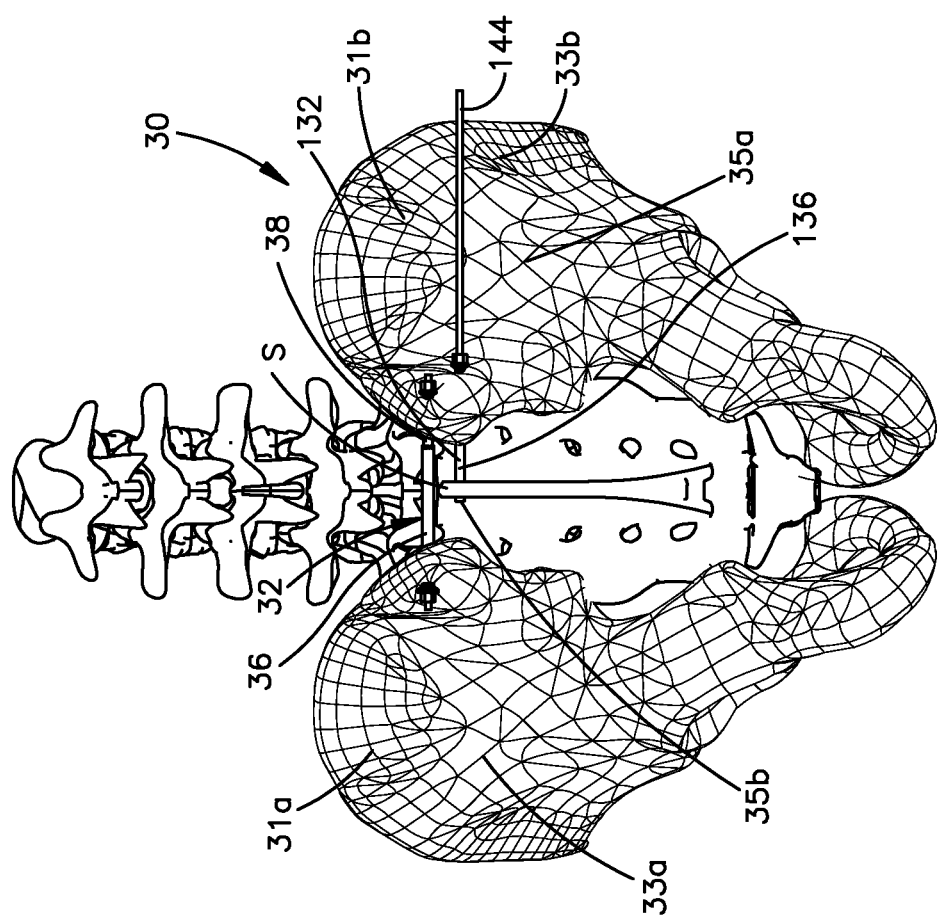
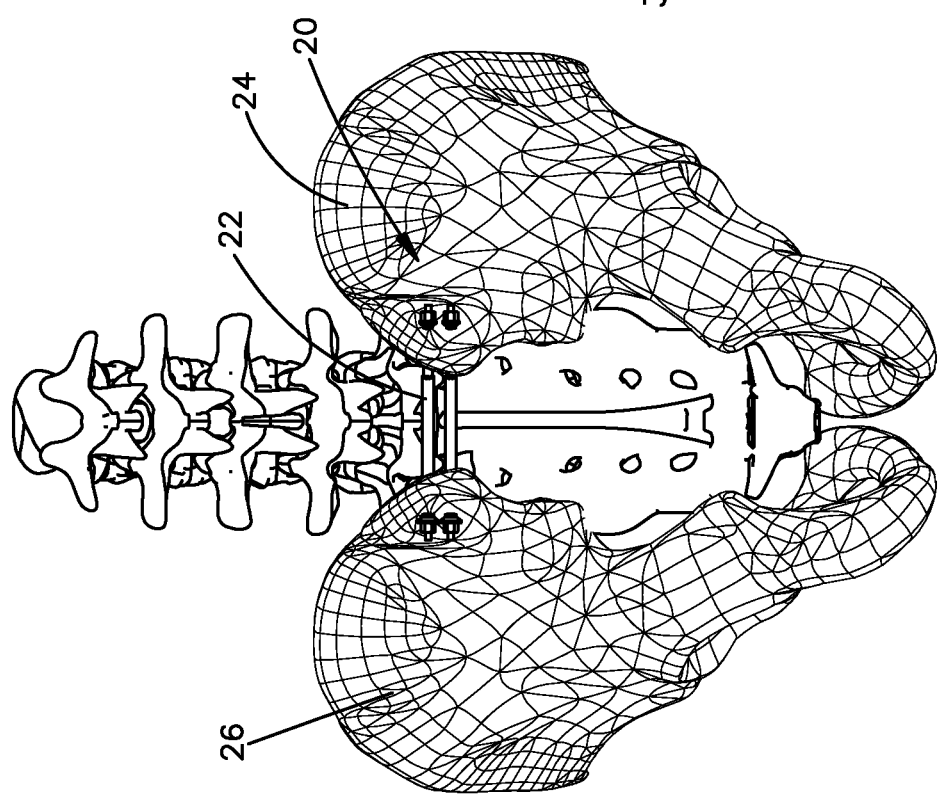

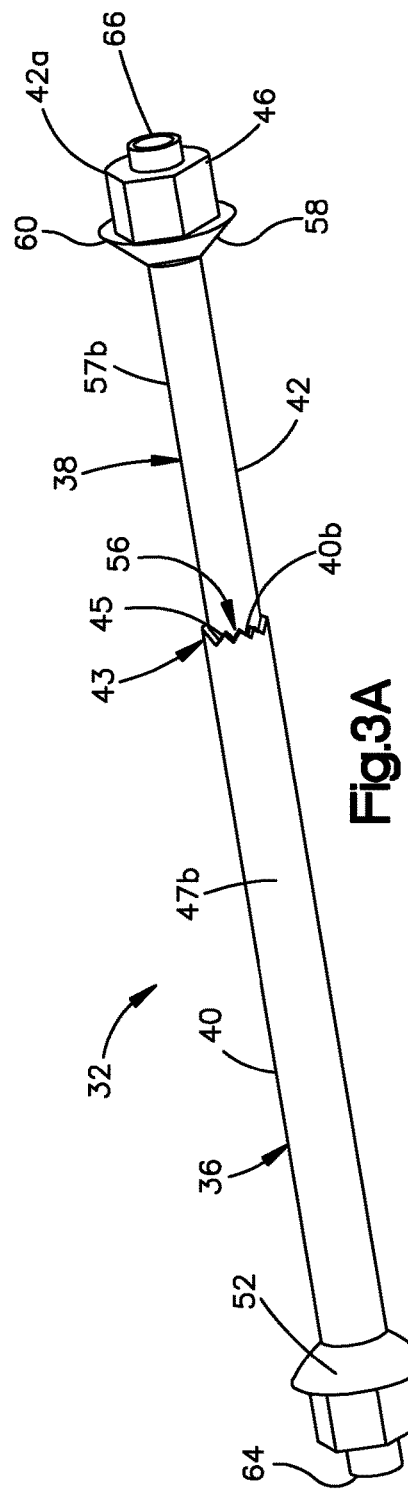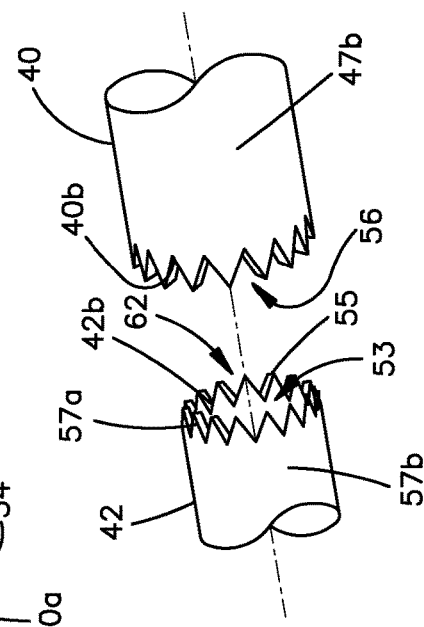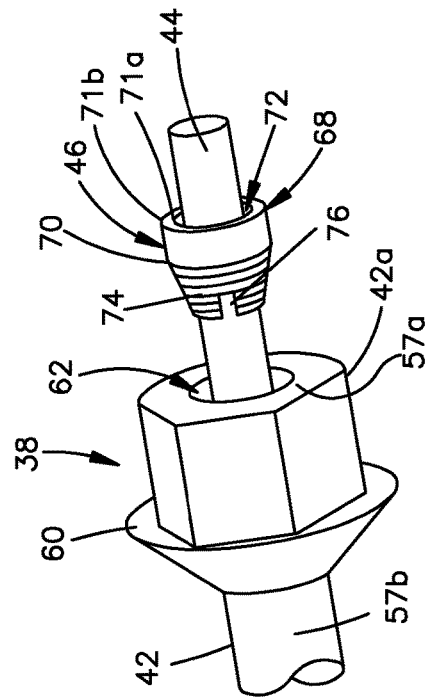

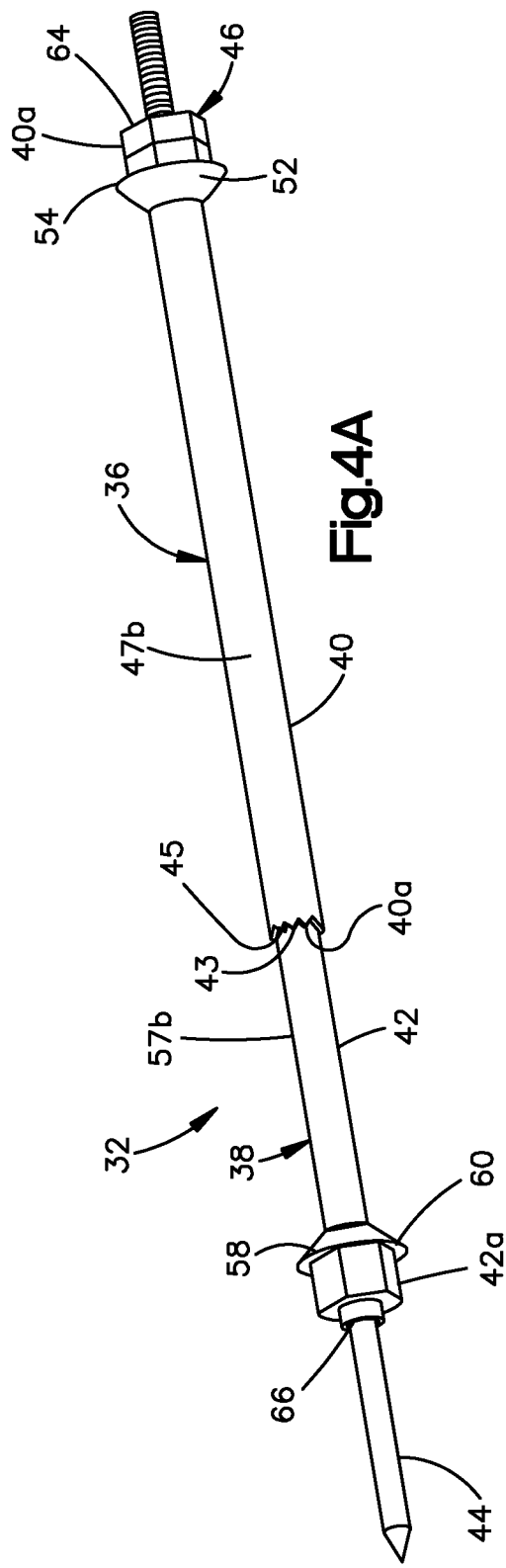
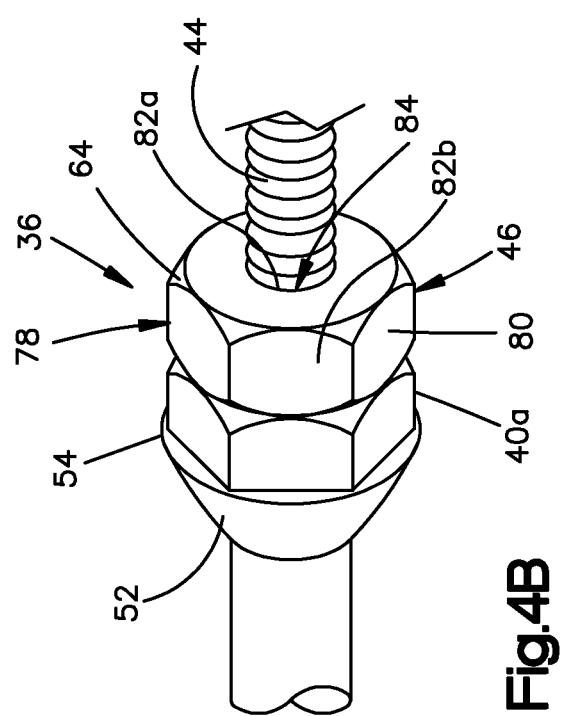

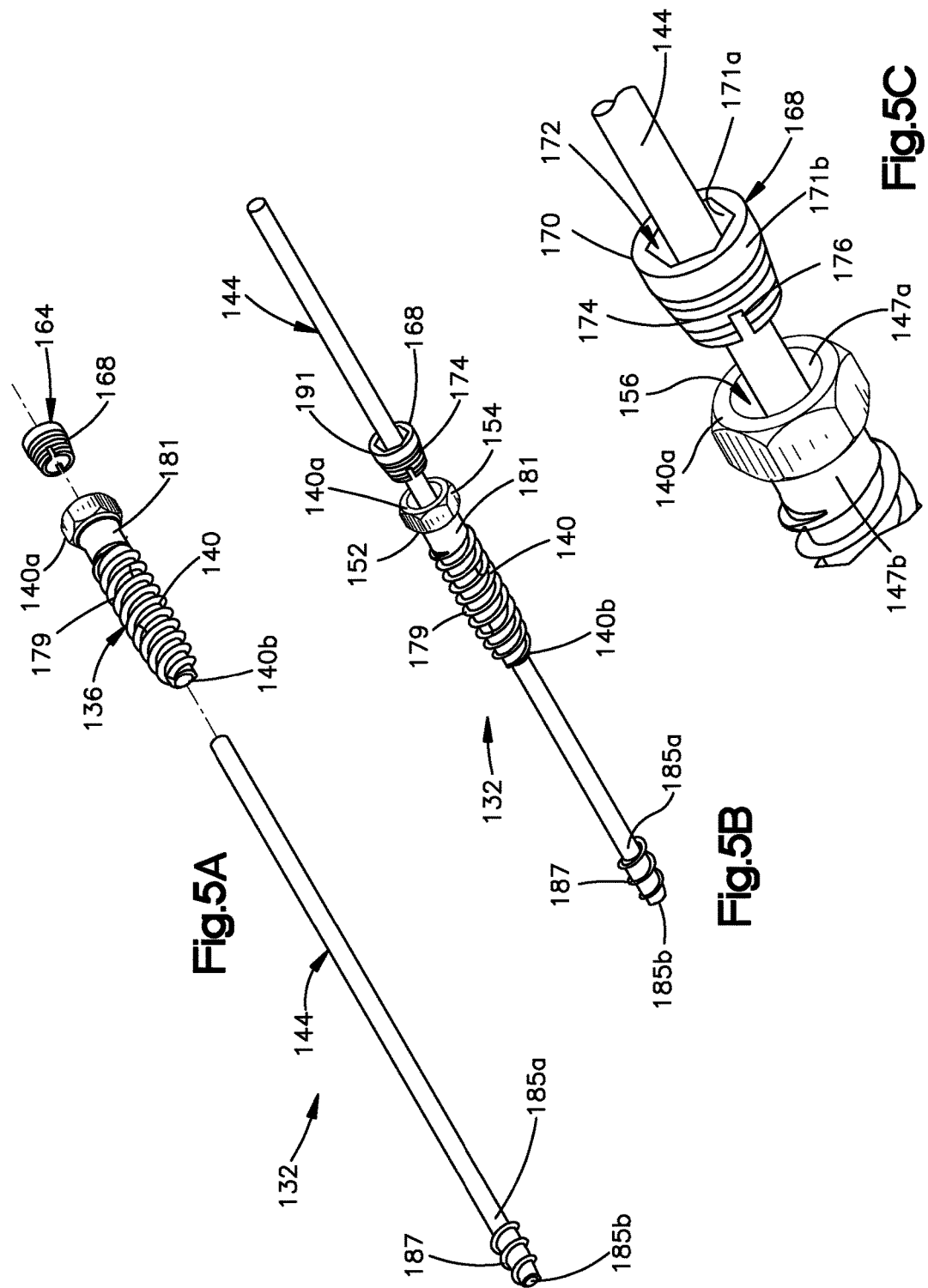

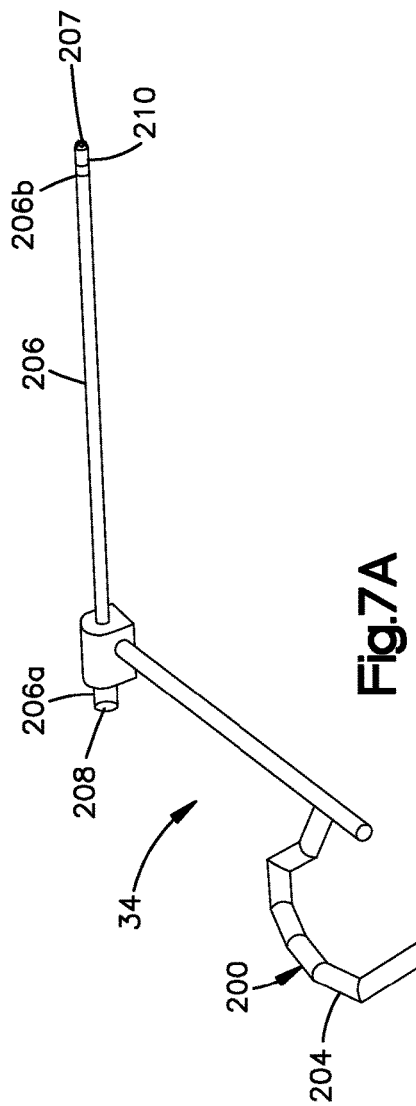
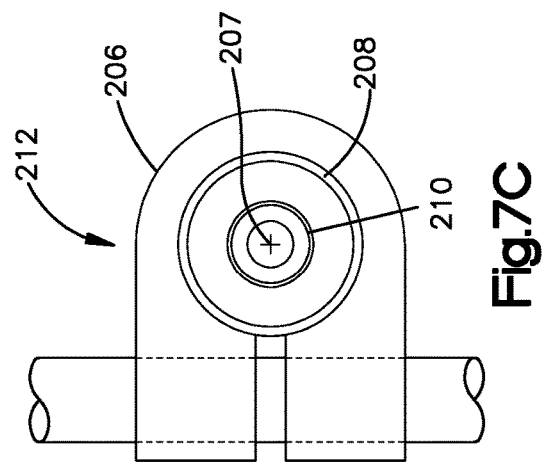
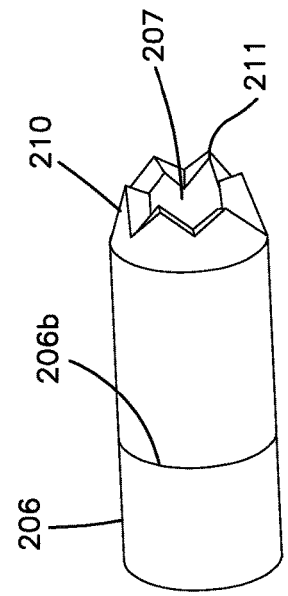
Fig.7A
Fig.7B
Fig.7C

SACRAL FIXATION SYSTEM

CROSS-REFERENCE TO RELATED APPLICATIONS

This claims priority to U.S. Patent Application Ser. No. 61/991,837 filed May 12, 2014, the disclosure of which is hereby incorporated by reference as if set forth in its entirety herein.

BACKGROUND

Implants for securing portions of a bone with respect to each other in order to promote bone healing are known. For instance, referring to FIG. 1, when a sacrum is fractured, conventional implant systems 20 such trans-iliac bars 22 are configured to support first and second ilium bones 24 and 26 with respect to each other, thereby stabilizing the sacral fracture. The trans-iliac bars 22 have a sufficient thickness to absorb the stresses experienced during use. While conventional trans-iliac bars 22 are suitable for their intended purpose, they have disadvantages because the surgeon cuts the ends after setting the bar into position. Due to the thickness of the trans-iliac bars 22, the surgical procedure typically involves a relatively large surgical field. Thus, the surgical procedure can be invasive, using a large incision in order to access the trans-iliac bars with a suitably robust cutting instrument.

SUMMARY

In a first aspect of the present disclosure, a sacral fixation implant can include an implant segment, a guide wire, and a locking member. The implant segment can include a shaft. The implant segment can define a proximal end and a distal end spaced from the proximal end in a distal direction. The implant segment can be configured to be inserted through an ilium bone in the distal direction. The implant segment can include an abutment surface that extends out from the shaft and is configured to abut the ilium bone so as to prevent further insertion of the shaft through the ilium bone. The guide wire can be configured to be received through the implant segment from the proximal end to the distal end, such that the guide wire extends out the distal end. The locking member is configured to fix the implant segment to the guide wire with respect to movement along the guide wire at least in a proximal direction opposite the distal direction.

BRIEF DESCRIPTION OF THE DRAWINGS

The foregoing summary, as well as the following detailed description of embodiments of the application, will be better understood when read in conjunction with the appended drawings. For the purposes of illustrating the methods, implants and systems of the present application, there is shown in the drawings preferred embodiments. It should be understood, however, that the application is not limited to the precise methods, implants, and systems shown. In the drawings:

FIG. 1 is a posterior view of a human sacral region and a conventional sacral implant system fixed to the sacral region;

FIG. 2 is am anterior view of a human sacrum and a sacral implant system constructed in accordance with one embodiment of the present disclosure fixed to the sacrum, the system including a first sacral fixation implant shown secured to first and second ilium bones; and a second sacral fixation implant shown secured to the first ilium bone and the sacrum;

FIG. 3A is a perspective view of a portion of the first sacral fixation implant illustrated in FIG. 2, the implant including first and second implant segments, and first and second locking members configured to secure the first and second implant segments to a guide wire;

FIG. 3B is a perspective view of distal ends of first and second implant segments of the implant illustrated in FIG. 3A;

FIG. 3C is a perspective view of a portion of the first implant segment illustrated in FIG. 3A, showing attachment of the first locking member;

FIG. 4A is a perspective view of a portion of a sacral fixation implant similar to the sacral fixation implant as illustrated in FIG. 3A, but including a locking member constructed in accordance with an alternative embodiment;

FIG. 4B is a perspective view of a portion of the first implant segment illustrated in FIG. 4A, but showing attachment of the locking member constructed in accordance with the alternative embodiment;

FIG. 5A is an exploded perspective view of the second sacral fixation implant illustrated in FIG. 2, showing an implant segment, a guide wire, and a locking member configured to secure the implant segment to the guide wire;

FIG. 5B is a perspective assembly view of the sacral fixation implant illustrated in FIG. 5A;

FIG. 5C is an enlarged perspective view of a portion of the sacral fixation implant illustrated in FIG. 5A, showing attachment of the locking member to the implant segment and the guide wire;

FIG. 7A is a perspective view of a targeting device constructed in accordance with one embodiment;

FIG. 7B is an enlarged perspective view of a cutting tip of the targeting device illustrated in FIG. 7A; and FIG. 7C is an end elevation view showing the targeting device aligned with an imaging source.

DETAILED DESCRIPTION

Figure 5D:
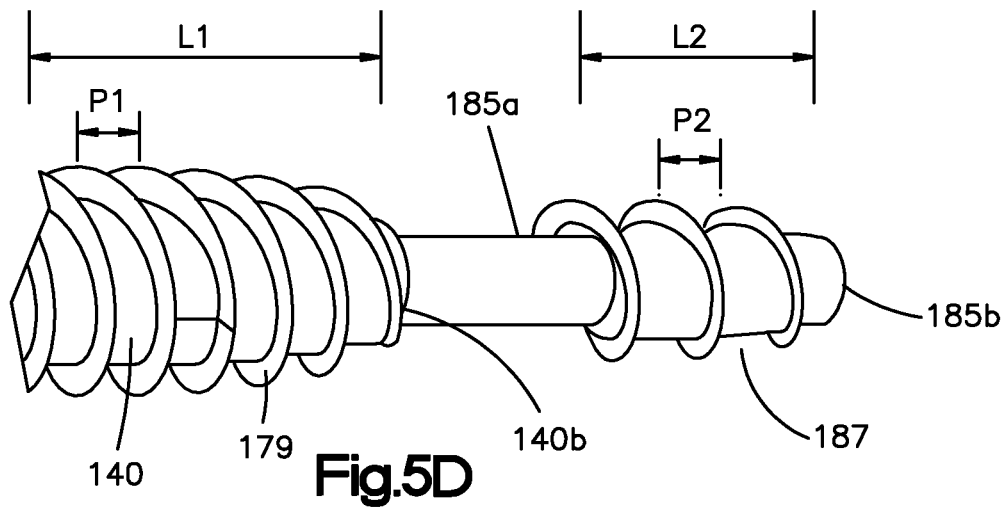
FIG. 5D is an enlarged perspective view of a portion of the sacral fixation implant illustrated in FIG. 5A, showing respective distal ends of the implant segment and the guide wire.
Figure 5E:
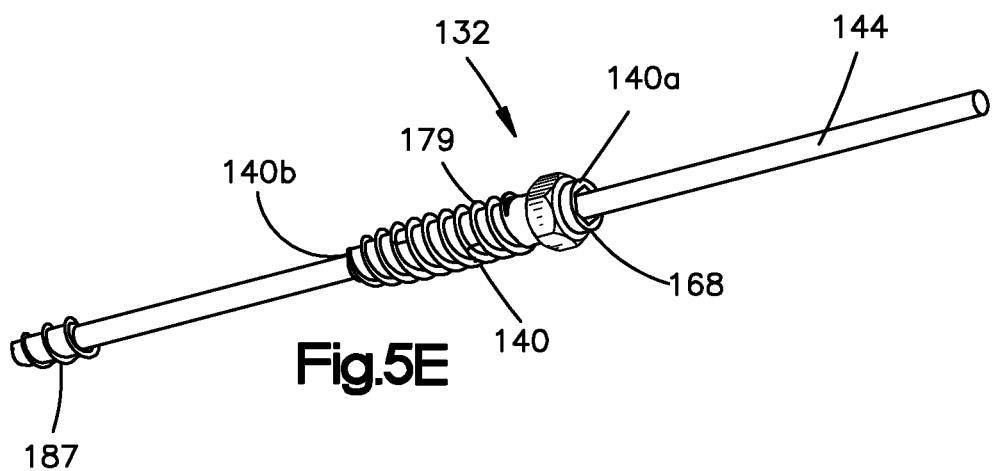
FIG. 5E is a perspective view of the sacral fixation implant illustrated in FIG. 5E, showing the locking member attached to the implant segment and the guide wire.

Referring to FIGS. 2 to 7C generally, a sacral fixation system 30 constructed in accordance with one embodiment includes one or more bone fixation implants, such as a first bone fixation implant 32 and a second bone fixation implant 132 configured to be fixed to respective first and second bone locations of a patient's body. For instance, the sacral fixation system can include a first bone fixation implant 20 that is configured to be fixed to respective first and second bone locations 31a and 31b, respectively. Additionally or alternatively, the sacral fixation system can include a second bone fixation implant 120 configured to be fixed to respective first and second bone locations 35a and 35b, respectively. In accordance with certain embodiments, the sacral fixation system 30 can further include a targeting device 34 configured to align a corresponding guide wire for insertion into or through the respective first and second bone locations of the bone fixation implants.

The first bone location 31a of the first implant 32, for instance, can be defined by a first ilium bone 33a, and the second bone location 31b can be defined by a second ilium bone 33b that is separated from the first ilium bone 33a by a sacrum S, and thus disposed on opposite sides of the sacrum S. Thus, the first bone fixation implant 32 can be referred to as a sacral fixation implant. For instance, the first ilium bone 33a can be defined by the left hip, and the second ilium bone 33b can be defined by the right hip. Alternatively, the first bone location 31a can be defined by the second ilium bone 33b, and the second bone location 31b can be defined by the first ilium bone 33a. In one example, the first implant 32 can extend through the first and second ilium bones 33a and 33b without passing through the sacrum S. Alternatively or additionally, the first implant 32 can extend through both the first and second ilium bones 33a and 33b, and further through the sacrum S. It will be appreciated that the first implant 32 is configured to stabilize the first and second ilium bones 33a and 33b so as to promote bone healing, for instance, in the event of a fracture of the sacrum S or other bone in the sacral region.

The first bone location 35a of the second implant 132 can be defined by an ilium bone, such as the second ilium bone 33b. Alternatively, the first bone location 35a can be defined by the first ilium bone 33a. The second bone location 35b can be defined by the sacrum S that is disposed between the first and second ilium bones 33a and 33b. Because the second bone implant 132 is configured to be implanted in the sacral region, the second bone fixation implant 132 can be referred to as a sacral fixation implant. It will be appreciated that the second implant 132 is configured to stabilize one of the first and second ilium bones 33a and 33b with respect to the sacrum S so as to promote bone healing, for instance, in the event of a fracture of the sacral region at a location between the sacrum S and the one of the first and second ilium bones 33a and 33b.

It will be appreciated that the first and second bone fixation implants 32 and 132 are configured to be implanted in accordance with minimally-invasive surgical (MIS) techniques, where small incisions are sufficient to facilitate implantation and fixation of the implant segments to the first and second bone locations. Each of the first and second implants 32 and 132 can be manufactured from any suitable material, for example, metals such as titanium or steel or polymers such as Polyetheretherkeytone (PEEK) or reinforced PEEK.

Referring now to FIGS. 2-4B, the first bone fixation implant 32 can include a first implant segment 36, which can include a first shaft 40. The first bone fixation implant 32 can further include a second implant segment 38, which can include a second shaft 42. The first bone fixation implant 32 can further include a guide wire 44. The guide wire 44 is configured to be received by each of the first and second implant segments 36 and 38 so as to guide each of the first and second implant segments 36 and 38 to the respective first and second bone locations 31a and 31b. In accordance with certain examples, the guide wire 44 is further configured to be secured to each of the first and second implant segments 36 and 38 so as to prevent movement of the first and second implants 36 and 38 away from each other. In other examples, the guide wire 44 is further configured to be secured to each of the first and second implant segments 36 and 38 so as to prevent movement of the first and second implants 36 and 38 toward from each other. The guide wire 44 can be configured as a Kirschner wire, or any suitable alternative guide wire as desired.

In use, the guide wire 44 can be driven through the first and second bone locations 31a and 31b. The first implant segment 36 is inserted over the guide wire 44 and driven through the first bone location 31a. In certain examples, the first implant segment 36 is configured to drill a bore hole through the first bone location 31a. Alternatively, the bore hole can be pre-drilled. The second implant segment 38 is inserted over the guide wire 44 and driven through the second bone location 31b. In certain examples, the second implant segment 38 is configured to drill a bore hole through the second bone location 31b. Alternatively, the bore hole can be pre-drilled. The second implant segment 38 is driven through the second bone location 31b until a distal end of the second implant segment 38 is received by the first implant segment 36.

The bone fixation implant 32 can further include a fixation mechanism 46 that is configured to secure the first and second implant segments 36 and 38 with respect to movement at least away from each other. In certain examples, the bone fixation the fixation mechanism 46 can be further configured to secure the first and second implant segments 36 and 38 with respect to movement toward each other. For instance, the fixation mechanism 46 can include the guide wire 44, and a first locking member 64 configured to fix the first implant segment 36 to the guide wire 44 with respect to movement at least away from the second implant segment 38. In certain examples, the first locking member 64 can be further configured to fix the first implant segment 36 to the guide wire 44 with respect to movement toward the second implant segment 38. The fixation mechanism 46 can further include a second locking member 66 that is configured to fix the second implant segment 38 to the guide wire 44 with respect to movement at least away from the first implant segment 36. In certain examples, the second locking member 66 can be further configured to fix the second implant segment 38 to the guide wire 44 with respect to movement toward the first implant segment 36.

Referring now to FIGS. 3A-4B, the first implant 32 can be constructed in accordance with any suitable embodiment. As described above, the first implant 32 can include the first implant segment 36 that, in turn, includes the first shaft 40 that is sized to be inserted through the first bone location 31a. The first shaft 40, and thus the first implant segment 36, can define a first proximal end 40a and a first distal end 40b opposite the first proximal end 40a. The first shaft 40 can be elongate along a first central axis between the first proximal end 40a and the first distal end 40b. At least a portion up to an entirety of the first central axis can be linear. The first shaft 40 can be cylindrical in shape, or can define any suitable alternative shape as desired.

The first implant segment 36 can further include a first abutment surface 52 that extends out from the first shaft 40. For instance, the first abutment surface 52 can be disposed proximate to the first proximal end 40a. In one example, the first implant segment 36 can include a first abutment member 54 that extends out from the first shaft 40. The first abutment member 54 can be raised with respect to the first shaft 40 away from the first central axis, such that the first abutment member 54 defines the first abutment surface 52. In this regard, it should be appreciated that the first abutment member 54 can be monolithic with the first shaft 40. Alternatively, the first abutment member 54, and the corresponding first abutment surface 52, can be separate from the first shaft 40 and attached to the first shaft 40. For instance, the first abutment member 54 can be in the form of a washer, clip, or other like structure that is configured to be supported by the first shaft 40 so as to define the first abutment surface.

Figure 6:
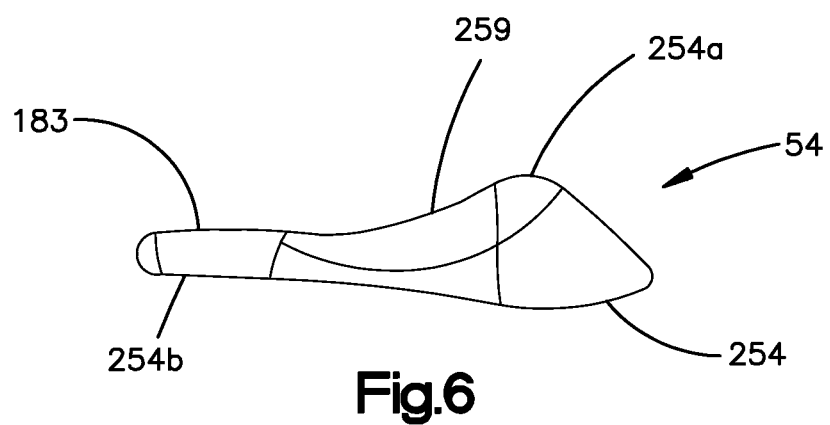
FIG. 6 is a perspective view of a washer configured to be included in accordance with the sacral fixation implants illustrated in FIGS. 3A-5E.

For instance, referring now to FIG. 6, the first abutment member 54 can be in the form of a washer 254 that defines an opening 259 that is sized to receive the first shaft 40, but sized smaller than the first proximal end 40*a*. Accordingly, the first proximal end 40*a* is configured to abut a first side 254*a* of the washer 254, such that a second side 254*b* of the washer 254 opposite the first side 254*a* defines the abutment surface. It is recognized that the central axis of the first shaft 40 might not be normal to the outer surface of the first bone location 31*a* when the first shaft 40 is inserted through the first bone location 31*a*. Accordingly, the washer 254 can be contoured such that the second side 254*b* rests against the outer surface of the first bone location 31*a* while the first side 254*a* generally conforms to the first proximal end 40*a*. For instance, a first end of the washer 254 can have a first thickness in the first direction, and a second end of the washer 254 can have a second thickness in the first direction that is greater than the first thickness. The first and second ends can, for instance, be disposed on opposed sides of the opening 259. It is appreciated that as the first proximal end 40*a* is tightened against the first bone location 31*a*, the washer 254 can remain stationary such that the proximal end 40*a* bears directly against the washer 254 as opposed to the first bone location 31*a*. In this regard, the washer 254 can define a fixation aperture that is configured to receive suture or other type of tether so as to fix the washer 254 to or adjacent soft tissue or bone as desired. Thus, the position of the washer 254 can be fixed and stabilized as the first shaft 40 is inserted through the first bone location 31*a*.

The first implant segment 36 can define a substantially constant first outer cross-sectional dimension from the distal end 40*b* to the first abutment surface 52. The first outer cross-sectional dimension extends through the first central axis, and can be a diameter or any suitable alternative cross-sectional dimension as desired. The first implant segment 36 can be annular. For instance, the first implant segment 36 can further define a first channel 56 that extends through the first shaft 40 from the first proximal end 40*a* to the first distal end 40*b*. The first channel 56 can extend along the first central axis. Thus, the first shaft 40 can define an inner surface 47*a* that defines the first channel 56, and an outer surface 47*b* opposite the inner surface 47*a*. The first channel 56 is sized to receive the guide wire 44.

In one example, referring to FIG. 3B, the first distal end 40*b* can define an annular tip 43 that can be serrated, such that the serrations extend out in the first direction from the first proximal end 40*a* toward the first distal end 40*b*. Accordingly, the annular tip defines a cutting surface 45 that is configured to drill a hole into the first bone location 31*a*. For instance, the cutting surface 45 can be placed against the first bone location 31*a* and the first shaft 40 can be rotated about the first central axis so that the serrated cutting surface 45 creates a bore hole in the first bone location 31*a*. Thus, the first shaft 40 can be referred to as self-drilling. As described above with respect to FIG. 2, the bone fixation implant 32 can be configured to extend through the sacrum S if desired. Accordingly, it should be appreciated, for instance when the implant 32 is to extend through the sacrum S, the cutting surface 45 can create bore hole in the sacrum after being driven through the first bone location 31*a*. Alternatively, a cutting instrument can create the bore hole in the first bone location 31*a* prior to insertion of the first shaft 40 through the first bone location 31*a*, as will be described in more detail below. The cutting instrument can further create the bore hole in the sacrum S if desired. Thus, it should be appreciated that the annular tip can alternatively define a smooth surface as desired.

Referring again to FIGS. 3A-4B, the second implant segment 38 can include the second shaft 42 that is sized to be inserted through the second bone location 31*b* as described above. The second shaft 42, and thus the second implant segment 38, can define a second proximal end 42*a* and a second distal end 42*b* opposite the second proximal end 42*a*. The second shaft 42 can be elongate along a second central axis between the second proximal end 42*a* and the second distal end 42*b*. At least a portion up to an entirety of the second central axis can be linear. The second shaft 42 can be cylindrical in shape, or can define any suitable alternative shape as desired. At least a portion of the second shaft 42 can be sized to be received in the first channel 56. For instance, at least the second distal end 42*b* can define a cross-sectional dimension that is slightly less than that of the first channel 56. When the second shaft 42 is received in the first channel 56, the first and second central axes can be coincident with each other.

The second implant segment 38 can include a second abutment surface 58 that extends out from the second shaft 42. For instance, the second abutment surface 58 can be disposed proximate to the second proximal end 42*a*. In one example, the second implant segment 38 can include a second abutment member 60 that extends out from the second shaft 42. The second abutment member 60 can be raised with respect to the second shaft 42 away from the second central axis, such that the second abutment member 60 defines the second abutment surface 58. In this regard, it should be appreciated that the second abutment member 60 can be monolithic with the second shaft 42. Alternatively, the second abutment member 60, and the corresponding second abutment surface 58, can be separate from the second shaft 42 and attached to the second shaft 42. For instance, the second abutment member 60 can be in the form of a washer, clip, or other like structure that is configured to be supported by the second shaft 42 so as to define the second abutment surface.

For instance, referring now to FIG. 6, the second abutment member 60 can be in the form of a washer 254 that defines an opening 259 that is sized to receive the second shaft 42, but sized smaller than the second proximal end 42*a*. Accordingly, the second proximal end 42*a* is configured to abut a first side 254*a* of the washer 254, such that a second side 254*b* of the washer 254 opposite the first side 254*a* defines the abutment surface. It is recognized that the central axis of the second shaft 42 might not be normal to the outer surface of the second bone location 31*b* when the second shaft 42 is inserted through the second bone location 31*b*. Accordingly, the washer 254 can be contoured such that the second side 254*b* rests against the outer surface of the second bone location 31*b* while the first side 254*a* generally conforms to the second proximal end 42*a*. For instance, a first end of the washer 254 can have a first thickness in the first direction, and a second end of the washer 254 can have a second thickness in the first direction that is greater than the first thickness. The first and second ends can, for instance, be disposed on opposed sides of the opening 259. It is appreciated that as the second proximal end 40*b* is tightened against the second bone location 31*b*, the washer 254 can remain stationary such that the second proximal end 40*b* bears directly against the washer 254 as opposed to the second bone location 31*b*. In this regard, the washer 254 can define a fixation aperture that is configured to receive suture or other type of tether so as to fix the washer 254 to or adjacent soft tissue or bone as desired. Thus, the position of the washer 254 can be fixed and stabilized as the second shaft 42 is inserted through the second bone location 31b.

The second implant segment 38 can define a substantially constant second outer cross-sectional dimension from the second distal end 42b to the second abutment surface 58. The second outer cross-sectional dimension extends through the second central axis, and can be a diameter or any suitable alternative cross-sectional dimension as desired. The second implant segment 38 can be annular. For instance, the second implant segment 38 can further define a second channel 62 that extends through the second shaft 42 from the second proximal end 42a to the second distal end 42b. Thus, the second shaft 42 can define an inner surface 57a that defines the second channel 62, and an outer surface 57b opposite the inner surface 57a. The second channel 62 can extend along the second central axis, and can have a cross-sectional dimension slightly greater than that of the guide wire 44, such that the second channel 62 is sized to receive the guide wire 44. Accordingly, the cross-sectional dimension of the second channel 62 is less than the cross-sectional dimension of at least a portion of the first channel 56 that receives the second shaft 42. The first and second cross-sectional dimensions can extend through the first and second central axes, respectively, and can define diameters or any suitable cross-sectional dimensions as desired.

In one example, as illustrated in FIG. 3B, the second distal end 42b can define a second annular tip 53 that can be serrated, such that the serrations extend out in the second direction from the second proximal end 42a toward the second distal end 42b. Accordingly, the second annular tip 53 defines a second cutting surface 55 that is configured to drill a hole into the second bone location 31b. For instance, the second cutting surface 55 can be placed against the second bone location 31b and the second shaft 42 can be rotated about the second central axis so that the serrated cutting surface 55 creates a bore hole in the second bone location 31b. Thus, the second shaft 42 can be referred to as self-drilling. As described above with respect to FIG. 2, the bone fixation implant 32 can be configured to extend through the sacrum S if desired. Accordingly, it should be appreciated, for instance when the implant 32 is to extend through the sacrum S, the second cutting surface 55 can create bore hole in the sacrum after being driven through the second bone location 31b. Alternatively, a cutting instrument can create the bore hole in the second bone location 31b prior to insertion of the second shaft 42 through the second bone location 31b, as will be described in more detail below. Thus, it should be appreciated that the second annular tip 53 can alternatively define a smooth surface as desired.

Referring now to FIGS. 2-4B, during operation, the guide wire 44 is placed across the sacroiliac joint from the first bone location 31a, such as the first ilium bone 33a, to the second bone location 31b, such as the second ilium bone 33b. Next, the first channel 56 receives the guide wire 44, and the first distal end 40b of the first shaft 40 is configured to be inserted through one of the first and second ilium bones 33a and 33b along the guide wire 44. For instance, the first shaft 40 can be inserted through the first bone location 31a in a first direction toward the second bone location 31b until the first abutment surface 52 abuts the first bone location 31a. The first channel 56 receives the guide wire 44, and advances along the guide wire 44, as the first shaft 40 is inserted through the first bone location 31a. Thus, the first abutment surface 52 is configured to abut the first bone location 31a so as to prevent further insertion of the first shaft 40 through the first bone location 31a.

The second distal end 42b of the second shaft 42 is configured to be inserted through the other of the first and second bone locations 31a and 31b. For instance, the second shaft 42 can be inserted through the second bone location 31b in a second direction, opposite the first direction, toward the first bone location 31a such that at least the second distal end 42b is received in the first channel 56 at a location between the first and second bone locations 31a and 31b. The second shaft 42 is inserted in the second direction, and the second distal end 42b is advanced in the first channel 56 toward the first proximal end 40a, until the second abutment surface 58 abuts the second bone location 31b. The second channel 62 receives the guide wire 44, and advances along the guide wire 44, as the second shaft 42 is inserted through the second bone location 31b, for instance, the second ilium bone 33b. Thus, the second abutment surface 58 is configured to abut the second bone location 31b so as to prevent further insertion of the second shaft 42 through the second bone location 31b. It should be appreciated that the first shaft 40 can be advanced through the first bone location 31a before, after, or simultaneously with, insertion of the second shaft 42 through the second bone location 31b, such that the second shaft is received by the first channel 56. Subsequent further insertion of the first shaft 40, the second shaft 42, or both, through the respective first and second bone locations 31a and 31b further advances the second distal end 42b in the first channel 56 in the second direction. As described above, the first and second shafts 40 and 42 can extend through the first ilium bone 33a and the second ilium bone 33b, respectively, without passing through the sacrum S. Alternatively, one or both of the first and second shafts can further extend through the sacrum S.

With continuing reference to FIGS. 3A-4B, and as described above, the fixation mechanism 46 is configured to fix the first and second implant segments 36 and 38 with respect to translation of the first and second implant segments 36 and 38 away from each other. It should be appreciated that mechanical interference between the first abutment surface 52 and the first bone location 31a fix the first implant segment 36 with respect to translation toward the second implant segment 38. Further, mechanical interference between the second abutment surface 58 and the second bone location 31b fixes the second implant segment 38 with respect to translation toward the first implant segment 36.

The fixation mechanism 46 can include the guide wire 44 and at least one locking member that is configured to prevent at least one of the first and second shafts 40 and 42 from moving away from the other of the first and second shafts 40 and 42. Thus, the at least one locking member can prevent movement of the at least one or both of the first and second shafts 40 and 42 along the guide wire in a direction from the respective distal end toward the respective proximal end. In certain examples, the at least one locking member can prevent movement of the at least one or both of the first and second shafts 40 and 42 along the guide wire in a direction from the respective proximal end toward the respective distal end. Further, it will be appreciated in certain examples that the at least one locking member does not extend through the implant from the first proximal end 40a to the second proximal end 42a. For instance, the fixation mechanism 46 can include first and second locking members 64 and 66. The first locking member 64 is configured to fix the first implant segment 36 to the guide wire 44 with respect to translation of the first implant segment 36 along the guide wire 44 in at least one direction, for instance in first and second opposed directions. The second locking member 66 is configured to fix the second implant segment 38 to the guide wire 44 with respect to translation of the second implant segment 38 along the guide wire 44 in at least one direction, for instance in first and second opposed directions. Thus, it should be appreciated that the guide wire 44 can be designed to remain permanently implanted in the sacral region. That is, the guide wire remains implanted with the first and second implant segments 36 and 38 after completion of the surgical procedure. Otherwise stated, the guide wire 44 can remain implanted as long as the first implant 32 remains implanted.

As illustrated in FIG. 3C, either or both of the first and second locking members 64 and 66 can be configured as a locking cap 68. The locking cap 68 includes a locking cap body 70 and a channel 72 that extends through the locking cap body 70. The channel 72 is sized to receive the guide wire 44. For instance, the locking cap body 70 includes an inner surface 71a that defines the channel 72, and an outer surface 71b opposite the inner surface 71a. The locking cap body 70 further defines at least one flexible wall 74 wall that defines a portion of the channel 72. For instance, the inner surface 71a at the flexible wall 74 defines the channel 72 having an initial cross-sectional dimension that is greater than that of the guide wire 44. The outer surface 71b at the flexible wall 74 can be threaded, and can further be tapered as it extends in a distal direction. The flexible wall 74 is configured to compress against the guide wire 44 in response to a radially compression force applied to the flexible wall 74. In one example, the locking cap 68 can further define at least one compression slot 76 that extends radially through the flexible wall 74 so as to be open to the channel 72.

Referring to FIG. 3C, the locking cap 68 will be described in connection with the second proximal end 42a of the second shaft 42. It will be appreciated, of course, that when the first locking member 64 is configured as a locking cap 68, the locking cap 68 can similarly cooperate with the first proximal end 40a of the first shaft 40 as described herein with respect to the second proximal end 42a of the second shaft 42. The locking cap 68, and in particular the flexible wall 74, can receive the guide wire 44, such that the guide wire 44 extends through the channel 72. The locking cap 68 can be translated along the guide wire 44 in the distal direction toward the second proximal end 42a. The flexible wall 74 is sized to be at least partially received in an aperture that extends through the second proximal end 42a in the second direction. The aperture can, for instance, be defined by the second channel 62 that extends through the second shaft 42 from the proximal end 42a to the distal end 42b. The first shaft 40 likewise includes an aperture that that extends through the first proximal end 40a along the first direction. The aperture can, for instance, be defined by the first channel 56 that extends through the first shaft 40 from the first proximal end 40a to the first distal end 40b. Accordingly, the inner surface 57a that defines the second channel 62 can further define the aperture. The inner surface 57a at the aperture is configured to apply the compression force to the flexible wall 74 as the locking cap is inserted into the aperture. The compression force applied by the inner surface 57a thus causes the flexible wall 74 to compress against the guide wire 44 and attach the locking cap 68 to the guide wire.

It is appreciated that the flexible wall 74 can be externally threaded, and the inner surface 57a can likewise be threaded. Accordingly, once the locking cap 68 has been translated along the guide wire 44 to a location whereby the flexible wall 74 contacts the second shaft 42, the locking cap 68 can be rotated relative to the second shaft 42 about the guide wire 44 so as to threadedly mate the cap 68 to the second shaft 42. Because the flexible wall 74 is tapered in the second direction, as the locking cap 68 is advanced in the aperture of the proximal end 42a, the inner surface 57a compresses the flexible wall 74 against the guide wire 44 as described above. It should be appreciated that, alternative or additionally, the inner surface 57a can be tapered in the second direction. Because the locking cap 68 threadedly mates with the respective shaft 40 or 42, when both of the first and second locking members 64 and 66 are configured as locking caps 68, the locking caps 68 fix the first and second shafts 40 and 42 to the guide wire 44 without applying a compressive force to the shafts 40 and 42 that would compress the first and second ilium bones 33a and 33b toward each other. Thus, when the sacrum S (see FIG. 2) is fractured, the fracture can be reduced with, for example, reduction forceps or any suitable alternative structure, and the threaded locking caps 68 can secure the first and second shafts 40 and 42 to the guide wire 44 so as to maintain the fracture in its reduced configuration, thereby promoting bone healing. Further, it should be appreciated that the locking cap 68 can be configured to prevent movement of the second implant segment 38 along the guide wire 44 both in a direction from the second distal end 42b toward the second proximal end 42a, and in a direction from the second proximal end 42a toward the second distal end 42b.

Referring now also to FIGS. 4A-4B, it should be appreciated that at least one of the first and second locking members 64 and 66 can be configured as a locking nut 78. For instance, the first locking member 64 can be configured as a locking cap 68, and the second locking member 66 can be configured as a locking nut 78. Alternatively, the first locking member 64 can be configured as a locking nut 78, and the second locking member 66 can be configured as a locking cap 68. Alternatively still, each of the first and second locking members 64 and 66 can be configured as a respective locking nut 78. Alternatively still, each of the first and second locking members 64 and 66 can be configured as a respective locking cap 68.

The locking nut 78 will be described in connection with the first proximal end 40a of the first shaft 40. It will be appreciated, of course, that when the second locking member 66 is configured as a locking nut 78, the locking nut 78 can similarly cooperate with the second proximal end 42a of the second shaft 42 as described herein with respect to the first proximal end 40a of the first shaft 40. The locking nut 78 can define a nut body 80 having an inner surface 82a that defines a channel 84 that extends through the nut body 80, and an outer surface 82b opposite the inner surface 82a. The channel 84 is sized to receive the guide wire 44. The inner surface 82 can be threaded. Thus, the locking nut 78 cab be said to be internally threaded. Further, at least a portion of the guide wire 44 can be externally threaded. The portion of the guide wire 44 can be disposed proximate to the first proximal end 40a, and can for instance extend from a first location spaced from the proximal end 40a in the second direction region to a second location spaced from the proximal end 40a in the first direction when the first abutment surface 52 is positioned adjacent the first bone location 31a.

As a result, the locking nut 78 is configured to be threaded onto the guide wire 44 and threadedly advanced along the guide wire 44 toward the first shaft 40 until the locking nut 78 abuts the first shaft 40. For instance, the locking nut 78 can abut the first proximal end 40a. Subsequent rotation of the locking nut 78 about the guide wire 44 while the second abutment surface 58 is in contact with the second bone location 31b therefore urges the first shaft 40 in the first direction toward the second shaft 42. Thus, when the first abutment surface 52 is in contact with the first bone location 31a, the compression nut is configured to apply a compressive force that is delivered to the first and second ilium bones 33a and 33b (see FIG. 2). In particular, the first shaft 40 extends through the first ilium bone 33a such that the first abutment surface 52 is in contact with the first ilium bone 33a, and the second shaft 42 extends through the is second ilium bone 33b and into the first shaft 40 until the second abutment surface 58 is in contact with the second ilium bone 33b. One of the first and second shafts 40 and 42 can be secured to the guide wire with respect to movement away from the other of the first and second shafts 40 and 42 in any manner described herein. The locking nut 78 is then advanced along the guide wire until it applies a compressive force to the other of the first and second shafts 40 and 42, thereby applying compression to each of the first and second ilium bones 33a and 33b toward the other of the first and second ilium bones 33a and 33b. When the sacrum S is fractured, the compression is used to promote bone healing. Since the implant 32 has the ability to maintain the compressive force throughout bone healing, the reduction of the fracture is maintained and bone healing promoted. As illustrated in FIG. 2, the sacral fixation system 30 can include first and second implants 32 which can each be constructed in accordance with any embodiment as described herein, and can be positioned at different locations at the ilium bones stabilize each of the ilium bones to each other, and in some examples to apply a compressive force to the sacrum S. It should be further appreciated that the fixation mechanism 46 can include at least one locking member that does not extend through the first and second shafts from the first proximal end to the second proximal end. For instance, the at least one locking member can be defined by one or both of the locking cap 68 and the locking nut 78.

While the first and second locking members 64 and 66 have been constructed in accordance with one embodiment, it is envisioned that the locking members 64 and 66 can be constructed in accordance with any suitable alternative embodiment that fixes the respective first and second implant segments 36 and 38 to the guide wire 44 with respect at least one or more up to all of 1) relative rotation about the central axis of the respective implant segment, 2) movement of the respective implant segment along the guide wire 44 toward the other implant segment, and 3) movement of the respective implant segment along the guide wire 44 away from the other implant segment. For instance either or both of the locking members 64 and 66 can be configured as a locking pin that extends through the implant segment and the guide wire 44, thereby fixing the implant segment to the guide wire 44. As another example, either or both of the locking members 64 and 66 can be configured as a set screw that is threadedly driven through a channel of the implant segment in a direction toward the respective central axis, and compresses against the guide wire 44. Thus, it will be appreciated that the first and second locking member 64 and 66 can be any suitably constructed locking member unless otherwise specified.

Once the locking members 64 and 66 are secured in place, the guide wire 44 can be severed at a location adjacent and proximal with respect to each of the first and second the locking members 64 and 66. Thus, the guide wire 44 can be severed at a location spaced from the first proximal end 40a in a proximal direction from the first distal end 40b to the first proximal end 40a. Further, the guide wire 44 can be severed at a location spaced from the second proximal end 42a in a proximal direction from the second distal end 42b to the second proximal end 42a. Because the guide wire 44 have a gauge that is substantially less than conventional trans-iliac bars, a simple cutting implement can cut the guide wire 44, as opposed to larger more robust cutting instruments that were required to cut the thicker trans-iliac bars. In this regard, it is appreciated that the anatomical loads are absorbed by the first and second implant segments 36 and 38, while the guide wire 44 assists in fixation of the first and second implant segments 36 and 38 with respect to movement away from and/or toward each other. The guide wire 44 can thus have a thickness substantially less than that of conventional trans-iliac bars. For instance, the guide wire can have any thickness as desired, for instance between 0.5 mm and 3.0 mm.

Referring now to FIGS. 2 and 5A-5E, the second bone fixation implant 132 is configured to stabilize one of the first and second ilium bone 33a and 33b with respect to the sacrum S. Thus, it should be appreciated that while FIG. 2 illustrates the second bone fixation implant 132 extends through the second ilium bone 33b, as is described in more detail below, the second bone fixation implant 132 can alternatively extend through the first ilium bone 33a. It should be further appreciated that a first one of the second bone fixation implant 132 can be inserted through the first ilium bone 33a and into the sacrum S, and a second one of the second bone fixation implant 132 can be inserted through the second ilium bone 33b and into the sacrum S. Thus, while the description below references implantation of the bone fixation implant 132 with respect to the second ilium bone 33b, the description applies equally to implantation of the bone fixation implant 132 with respect to the first ilium bone 33a. In this regard, the first bone location 35a can refer to either the first ilium bone 33a or the second ilium bone 33b.

The second bone fixation implant 132 includes an implant segment 136 that includes a shaft 140. The shaft 140, and thus the implant segment 136, defines a proximal end 140a and a distal end 140b spaced from the proximal end in a distal direction. The shaft 140 can be elongate along a central axis from the proximal end 140a to the distal end 140b. At least a portion up to an entirety of the central axis can be linear. The proximal end 140a can be raised with respect to the distal end 140b. Thus, the proximal end can extend out from the central axis a first distance in a direction perpendicular to the distal direction, and the distal end 140b can extend out from the central axis a second distance in the direction perpendicular to the first direction that is less than the first distance. The implant segment 136 defines a channel 156 that extends through the shaft 140 from the proximal end 140a to the distal end 140b. The implant segment 136 is configured to be inserted through the first bone location 35a in the distal direction. The implant segment 136 can further include an abutment surface 152 that extends out from the shaft 140 and is configured to abut the respective ilium bone so as to prevent further insertion of the shaft 140 through the ilium bone. As described above, the abutment surface 152 can be defined by an abutment member 154 that can be monolithic with the shaft. For instance, the abutment surface 152 can be defined by the proximal end 140a, which can define the abutment member 154. Alternatively, the abutment member 154, and the corresponding abutment surface 152, can be separate from the shaft 140 and attached to the shaft 140. For instance, the abutment member 154 can be in the form of a washer, clip, or other like structure that is configured to be supported by the first shaft 40 so as to define the first abutment surface.

For instance, referring now to FIG. 6, the abutment member 154 can be in the form of a washer 254 that defines an opening 259 that is sized to receive the shaft 140, but sized smaller than the first proximal end 140a. Accordingly, the proximal end 140a is configured to abut a first side 254a of the washer 254, such that a second side 254b of the washer 254 opposite the first side 254a defines the abutment surface. It is recognized that the central axis of the shaft 140 might not be normal to the outer surface of the first bone location 35a when the shaft 140 is inserted through the first bone location 35a. Accordingly, the washer 254 can be contoured such that the second side 254b rests against the outer surface of the first bone location 35a while the first side 254a generally conforms to the proximal end 140a. For instance, a first end of the washer 254 can have a first thickness in the first direction, and a second end of the washer 254 can have a second thickness in the first direction that is greater than the first thickness. The first and second ends can, for instance, be disposed on opposed sides of the opening 259. It is appreciated that as the first proximal end 40a is tightened against the first bone location 35a, the washer 254 can remain stationary such that the proximal end 140a bears directly against the washer 254 as opposed to the first bone location 35a. In this regard, the washer 254 can define a fixation aperture that is configured to receive suture or other type of tether so as to fix the washer 254 to or adjacent soft tissue or bone as desired. Thus, the position of the washer 254 can be fixed and stabilized as the shaft 140 is inserted through the first bone location 35a.

With continuing reference to FIGS. 2 and 5A-5E, implant 132 can include at least one first external thread 179 that extends out from the shaft 140. Otherwise stated, the shaft 140 can define at least one external thread 179. The at least one first external thread 179 can extend along the shaft 140 in the distal direction from a location adjacent to the proximal end 140a. The at least one first external thread 179 can further extend along the shaft 140 in the proximal direction from the distal end 140b to the location adjacent to the proximal end 140a. For instance, the at least one first external thread 179 can be spaced from the proximal end 140a in the distal direction. In one example, the shaft can define an unthreaded neck 181 that is disposed between the proximal end 140a and the at least one first external thread 179. Thus, the at least one external thread 179 can extend from the distal end 140b to the neck 181. The at least one first external thread 179 is configured to be driven at least into the first bone location 35a in the distal direction. For instance, the at least one first external thread 179 is configured to be driven through the first bone location 35a, such that the first bone location 35a is captured between the proximal end 140a and the at least one first external thread 179. Thus, the unthreaded neck 181 is configured to receive the first bone location 35a after the at least one first external thread 179 has passed through the first bone location 35a. In one example, the at least one first external thread 179 can be self-tapping. In a further example, the at least one external thread 179 can be self-drilling.

The fixation implant 132 can further include a guide wire 144 that is configured to be received through the implant segment 136. For instance, the guide wire 144 is configured to extend through the channel 156 from the proximal end 140a to the distal end 140b, such that the guide wire 144 extends out the distal end 140b. The guide wire 144 defines a distal portion 185a that defines a distal end 185b. The guide wire 144 is configured to be received by the channel 156 such that the distal portion 185a extends out the distal end 185a in the distal direction. Thus, the guide wire 144 can extend through the channel 156 such that the distal end 185b of the guide wire 144 is spaced from the distal end 140b of the shaft 140 in the distal direction. The guide wire 144 can be configured as a Kirschner wire of the type described above with respect to the guide wire 44.

The guide wire 144 can define at least one second external thread 187 that extends along at least a length of the distal portion 185a. For instance, the at least one second external thread 187 can extend from the distal end 185b in a proximal direction that is opposite the distal direction. The at least one second external thread 187 is configured to be driven at least into the second bone location 135b in the distal direction. Thus, it should be appreciated that the guide wire 44 is designed to remain permanently implanted in the sacral region. That is, the guide wire remains implanted with the first and second implant segments 36 and 38 after completion of the surgical procedure. Otherwise stated, the guide wire 44 can remain implanted as long as the first implant 32 remains implanted.

In one example, the at least one second external thread 187 can be self-tapping. In a further example, the at least one second external thread 187 can be self-drilling. The at least one first external thread 179 can define a first maximum outer diameter, such that no other location of the at least one first external thread 179 has a diameter greater than that of the first maximum outer diameter. Similarly, the at least one second external thread 187 can define a second maximum outer diameter, such that no other location of the at least one second external thread 187 has a diameter greater than that of the second maximum outer diameter. In one example, the second maximum outer diameter is no greater than the first maximum outer diameter. For instance, the second maximum outer diameter can be less than the first maximum outer diameter. Otherwise stated, the first maximum outer diameter can be greater than the second maximum outer diameter. Accordingly, the at least one second external thread 187 can pass through the first bone location 35a, and the at least one first external thread 179 can subsequently threadedly purchase in the first bone location 35a as the shaft 140 is driven in the distal direction through the first bone location 35a.

The at least one first external thread 179 can define a first length L1 in the distal direction. The at least one second external thread 187 can define a second length L2 in the distal direction. In one example, the second length L2 can be less than the first length L1. Accordingly, it should be appreciated that the at least one first thread 179 can be driven into first bone location 35a prior to driving the at least one second thread 187 into second bone location 35b. Alternatively, the at least one second thread 187 can be driven into the second bone location 35b prior to driving the at least one first thread 179 into the first bone location 35a. Alternatively still, the bone implant 132 can define a distance between the at least one first thread 179 and the at least one second thread in the distal direction that is substantially equal to a distance from the first bone location 35a and the second bone location 35b prior to simultaneous fixation of each of the at least one first and second external threads 179 and 187, respectively, into the first and second bone locations 35a and 35b.

The implant 132 can further include at least one locking member 164 that is configured to fix the implant segment 136 to the guide wire 144 with respect to rotation about the guide wire 144. In one example, the locking member 164 can be configured to fix the implant segment 136 to the guide wire 144 with respect to movement along the guide wire 144 in the proximal direction. In another example, the locking member 164 can be configured to fix the implant segment 136 to the guide wire 144 with respect to movement along the guide wire 144 in the distal direction.

The locking member 164 can be configured as a locking cap 168. The locking cap 168 includes a locking cap body 170 and a channel 172 that extends through the locking cap body 170. The channel 172 is sized to receive the guide wire 144. For instance, the locking cap body 170 includes an inner surface 171a that defines the channel 172, and an outer surface 171b opposite the inner surface 171a. The locking cap body 170 further defines at least one flexible wall 174 wall that defines a portion of the channel 172. For instance, the inner surface 171a at the flexible wall 174 defines the channel 172 having an initial cross-sectional dimension that is greater than that of the guide wire 144. The outer surface 171b at the flexible wall 174 can be threaded, and can further be tapered as it extends in a distal direction. The flexible wall 174 is configured to compress against the guide wire 144 in response to a radially compression force applied to the flexible wall 174 toward the central axis of the implant segment 136. In one example, the locking cap 168 can further define at least one compression slot 176 that extends radially through the flexible wall 174 so as to be open to the channel 172.

The locking cap 168, and in particular the flexible wall 174, can receive the guide wire 144, such that the guide wire 144 extends through the channel 172. The locking cap 168 can be translated along the guide wire 144 in the distal direction toward the proximal end 140a. The flexible wall 174 is sized to be at least partially received in an aperture that extends through the proximal end 140a in the second direction. The aperture can, for instance, be defined by the channel 156 that extends through the shaft 140 from the proximal end 140a to the distal end 140b. The implant segment 136 includes an inner surface 147a that defines the channel 156, and an outer surface 147b opposite the inner surface 147a. It is appreciated that the at least a portion of the outer surface 147b can define the at least one first external thread 179. The inner surface 147a can further define the aperture. Otherwise stated, the channel 156 can include the aperture. The inner surface 147a at the aperture is configured to apply the compression force to the flexible wall 174 as the locking cap 168 is inserted into the aperture. The compression force applied by the inner surface 147a thus causes the flexible wall 174 to compress against the guide wire 144 and secure the locking cap 168 to the guide wire 144. For instance, the locking cap 168 can compress against the guide wire 144 at a location that is not offset from the abutment surface 152 in the distal direction. In one example, the locking cap 168 can compress against this guide wire 144 at a location offset from the abutment surface 152 in the proximal direction.

It is appreciated that the flexible wall 174 can be externally threaded, and the inner surface 147a can likewise be threaded. For instance, the inner surface 147 can be threaded at the proximal end 140a. Accordingly, once the locking cap 168 has been translated along the guide wire 144 to a location whereby the flexible wall 174 contacts the shaft 140, the locking cap 168 can be rotated relative to the shaft 140 about the guide wire 144 so as to threadedly mate the locking cap 168 to the shaft 140. At least one of the flexible wall 174 and the inner surface 147a at the proximal end 140a can be tapered in the distal direction. Accordingly, as the locking cap 168 is advanced in the aperture at the proximal end 140a, the inner surface 147a compresses the flexible wall 174 against the guide wire 144 as described above. Because the locking cap 168 threadedly mates with the shaft 140, the locking caps 168 can fix the shaft 140 to the guide wire 144 without applying a compressive force to the shaft 140 that would urge the implant segment 136 to move along the guide wire 144 in the distal direction.

With continuing reference to FIGS. 2 and 5A-5E, the at least one first external thread 179 can define a first pitch P1, and the at least one second external thread 187 can define a second pitch P2 that is greater than the first pitch P1. Accordingly, when the locking member 164 secures the implant segment 136 to the guide member, such as the guide wire 144, and the at least one first external thread 179 is simultaneously driven into the first bone location 35a while the at least one second external thread 187 is driven into the second bone location 35b, the at least one first external thread 179 can advance through the first bone location 35a in the distal direction at a first rate, and the at least one second external thread 187 can advance through the second bone location 35b in the distal direction at a second rate that is greater than the first rate. Accordingly, the difference between the first thread pitch P1 and the second thread pitch P2 can cause one or both of the first and second bone locations 35a and 35b to be drawn toward the other of the first and second bone locations 35a and 35b when the locking member 164 secures the implant segment 136 to the guide member, such as the guide wire 144, and the at least one first external thread 179 is simultaneously driven into the first bone location 35a while the at least one second external thread 187 is driven into the second bone location 35b. Thus, the implant 132 is configured to apply a compressive force that is delivered to the first and second bone locations 35a and 35b. When the sacrum region defines a bone fracture at a location between the first and second bone locations 35a and 35b, the compression is used to promote bone healing. For instance, the compression can reduce the fracture, drawing the bone segments opposite the fracture toward and against each other.

Alternatively, it is appreciated that the first pitch P1 and the second pitch P2 can be substantially equal to each other. Accordingly, when the locking member 164 secures the implant segment 136 to the guide member, such as the guide wire 144, and the at least one first external thread 179 is simultaneously driven into the first bone location 35a while the at least one second external thread 187 is driven into the second bone location 35b, the first and second rates can be equal. Thus, when the sacral region defines a bone fracture at a location between the first and second bone locations 35a and 35b, the fracture can be reduced with, for example, reduction forceps or any suitable alternative structure, and the locking member 146 can secure the shaft 140 to the guide wire 144 so as to maintain the fracture in its reduced configuration, thereby promoting bone healing.

While the locking member 164 has been constructed in accordance with one embodiment, it is envisioned that the locking member 164 can be constructed in accordance with any suitable alternative embodiment that fixes the implant segment 136 to the guide wire 144 with respect at least one or more up to all of 1) relative rotation about the central axis of the implant segment 136, 2) movement of the implant segment 136 along the guide wire in the proximal direction, and 3) movement of the implant segment 136 along the guide wire in the distal direction. For instance the locking member 164 can be configured as a locking pin that extends through the implant segment 136 and the guide wire, thereby fixing the implant segment 136 to the guide wire 144. As another example, the locking member 164 can be configured as a set screw that is threadedly driven through a channel of the implant segment 136 in a direction toward the respective central axis, and compresses against the guide wire 144.

Thus, it will be appreciated that the locking member 146 can be any suitably constructed locking member unless otherwise specified.

Once the locking member 164 secures the shaft 140 to the guide wire 144, the guide wire 44 can be severed at a location adjacent spaced from the location where the locking member 164 is attached to the guide wire in the proximal direction. Because the guide wire 144 have a gauge that is substantially less than conventional trans-iliac bars, a simple cutting implement can cut the guide wire 144, as opposed to larger more robust cutting instruments that were required to cut the thicker trans-iliac bars. In this regard, it is appreciated that anatomical loads are shared by the shaft and the guide wire 144. The guide wire 144 can thus have a thickness substantially less than that of conventional trans-iliac bars. For instance, the guide wire can have any thickness as desired, for instance between 0.5 mm and 3.0 mm.

It is appreciated that a method can be provided for stabilizing an ilium bone 33a or 33b with respect to the sacrum bone S that is spaced from the ilium bone by a first distance. The method can include the steps of inserting the guide wire 144 through the shaft 140 of the implant segment 136. As described above, the shaft 140 can define the at least one first external thread having 179 that has the first pitch P1, and the guide wire 144 can define the at least one second external thread 187 that has the second pitch greater than the first pitch P1. The inserting step can cause the at least one second external thread 187 to be spaced from the at least one first external thread 179 in the distal direction. The method can further include the step of simultaneously driving 1) the at least one first external thread 179 at least into the ilium bone 33a or 33b, and 2) the at least one second external thread 187 at least into the sacrum bone S, thereby causing the sacrum bone S to be spaced from the ilium bone a second distance less than the first distance. For instance, the thread 187 can terminate in the sacrum bone S without extending through the sacrum bone S. Alternatively, the second external thread 187 can extend through the sacrum bone S. It should be appreciated in one example that when the thread 187 extends through the sacrum bone S, the guide wire 144 does not extend through the sacrum bone S such that the thread 187 extends into the ilium bone 33a. For instance, when the thread 187 extends through the sacrum bone S, a portion of the thread 187 remains purchased with the sacrum bone S.

The method can further include the step of rotatably coupling the implant segment 136 to the guide wire 144 prior to the driving step, as described above. For instance, the step of rotatably coupling can include fixing the locking member 146 to both the implant segment 136 and the guide wire 144 with respect to relative rotation. For instance, the step of rotatably coupling can include inserting the locking member 146 into the aperture of the implant segment 136, such that the inner surface 147a of the implant segment 136 that defines the aperture urges the flexible wall 174 of the locking member 146 against the guide wire 144. The inserting step can further include the step of threadedly mating the inner surface 147a and the outer surface 171b of the flexible wall 174, as described above. The method can further include the step of, prior to the step of rotatably coupling, driving the implant segment 136 along the guide wire 144 such that the at least one first external thread 179 is spaced from the at least one second external thread 187 a predetermined distance before securing the locking member 164 to the implant segment 136 and the guide wire 144. For instance, the at least one first external thread 179 is spaced from the at least one second external thread 187 a distance such that a distalmost end of the at least one first external thread 179 and a distalmost end of the at least one second external thread 187 are spaced from each other in the distal direction a distance substantially equal to the first distance. Thus, the at least one first external thread 179 can enter the first bone location 35a as the at last one second external thread 187 enters the second bone location 35b when the locking member 146 is secured to the implant segment 136 and the guide wire 144. Alternatively, the distalmost end of the at least one first external thread 179 and a distalmost end of the at least one second external thread 187 can be spaced from each other a distance along the distal direction that is less than the first distance. Thus, the at least one first external thread 179 can enter the first bone location 35a before the at last one second external thread 187 enters the second bone location 35b. Alternatively still, the distalmost end of the at least one first external thread 179 and a distalmost end of the at least one second external thread 187 can be spaced from each other a distance in the distal direction that is greater than the first distance. Thus, the at least one first external thread 179 can enter the first bone location 35a after the at last one second external thread 187 enters the second bone location 35b.

The driving step comprises applying a torsional force to the implant segment 136. For instance, the implant segment 136 can include a driving interface 191 that can be defined by the outer surface 147b or the inner surface 147a. In one example, the proximal end 140a of the shaft can define the driving interface 191. The driving interface 191 is configured to mate with a driving end of a driving instrument that is configured to apply a torsional force to the implant segment 136. Because the implant segment 136 is fixed to the guide wire 144 with respect to rotation, the torsional force can drive both the implant segment 136 and the guide wire 144 to simultaneously rotate. Alternatively, separate torsional forces can be applied to the implant segment 136 and the guide wire 144 that independently drive the implant segment and the guide wire 144 to rotate. In one example, the separate torsional forces can be applied to the implant segment 136 and the guide wire 144 that independently drive the implant segment and the guide wire 144 to rotate at the same rate. Alternatively still, the torsional force can be applied directly to the guide wire 144, such that the implant segment 136 rotates simultaneously with the guide wire 144. The driving step can be performed until the abutment surface 152 abuts the ilium bone, thereby preventing the implant segment 136 from being further driven into the ilium bone. When the driving step is completed, at least a portion of the at least one second external thread 187 can remain embedded in the sacrum S, or can be spaced from the sacrum S in the distal direction. Similarly, when the driving step is completed, at least a portion of the at least one first external thread 179 can remain embedded in the ilium bone, or can be spaced from the ilium bone in the distal direction. The implant segment 136 can be coupled to the guide wire at an attachment location as described above, and the method can further include the step of severing the guide wire 144 at a cut location spaced from the attachment location in a proximal direction. In one example, the cut location can be spaced from the proximal end 140a in the proximal direction.

Referring now to FIGS. 2 and 7A-C, and as described above, the sacral fixation system 30 can include a drilling instrument configured to create bore holes in either or both of the first and second bone locations 31a and 31b. The sacral fixation system 30 can further include a targeting device 34 that can be configured as an alignment guide 200 configured to guide the guide wire 44 through the first and second bone locations 31a and 31b. Similarly, the targeting device 34 that can be configured as an alignment guide 200 configured to guide the guide wire 44 through the first and second bone locations 35a and 35b. The alignment guide 200 can include a support base 202, and a positionally adjustable arm 204. The alignment guide 200 can further include an elongate guide member 206 that defines a proximal end 206a and a distal end 206b spaced from the proximal end along a central axis, that is configured to be coincident with the first and second central axes of the implant segments described above. The alignment guide 200 can define a channel 207 that extends through the guide member 206 from the proximal end 206a to the distal end 206b. The central axis of the guide member 206 can define the central axis of the channel 207. The guide member 206 includes a radio opaque marker 208 at the proximal end 206a. For instance, the radio-opaque marker 208 can be configured as an annular ring that receives the proximal end 206a. The guide member 206 can further include a radio-opaque tip 210 that extends from the distal end 206b. The channel 207 can further extend through the tip 210 and the marker 208. The tip 210 can include one or more teeth 211 configured to embed into either or both of the first and second bone locations 31a and 31b, or the first bone location 35a. The guide member 206 can be supported by the adjustable arm 204 so as to be positionally adjustable, as will now be described.

In particular, it is recognized that it is desirable for the central axis of the guide member 206 to be aligned with the first and second bone locations. Thus, the guide member 206 is configured to provide an indication as to whether the central axis is aligned with the first and second bone locations 31a and 31b, or 35a and 35b, on a radiographic image 212. The radiographic image, for instance, can be an X-Ray. In this regard, it is recognized that a visual inspection of the tip 210 might initially appear to be aligned with the first and second bone locations, even though the central axis of the guide member 206 is not in alignment with the first and second bone locations 31a and 31b. The radio-opaque marker 208 and the radio-opaque tip 210 are configured to be disposed in a predetermined position with respect to each other in the radiographic image 212, indicating that the radio-opaque marker 208 and the radio-opaque tip 210 are aligned with each other. Accordingly, when the radio-opaque marker 208 and the radio-opaque tip 210 are aligned with each other on the radiographic image 212, and the channel 207 is aligned with each of the first and second bone locations, then it can be concluded that the central axis of the guide member 206 is aligned with the first and second bone locations. For instance, the predetermined position between the radio-opaque marker 208 and the radio-opaque tip 210 can be a concentric relationship. In one example, the tip 210 can be concentrically disposed within the radio-opaque marker 208.

If the radio-opaque marker 208 and the radio-opaque tip 210 are not aligned with each other on the radiographic image 212, the guide member 206 can be positionally adjusted until the radio-opaque marker 208 and the radio-opaque tip 210 are aligned with each other. If the radio-opaque marker 208 and the radio-opaque tip 210 are aligned with each other, but the central axis or channel 207 is not aligned with each of the first and second bone locations 31a and 31b, the guide member 206 can be positionally adjusted until the radio-opaque marker 208 and the radio-opaque tip 210 are aligned with each other, and the central axis or channel 207 are aligned with each of the first and second bone locations. Next, the teeth 211 can be anchored in either of the first and second bone locations 31a and 31b, or the first bone location 35a, while the guide member 206 is in the aligned configuration. The guide wire 44 can then be introduced through the channel 207 and through the first and second bone locations 31a and 31b alone or in combination with the sacrum S as desired. In this regard, it should be appreciated that the guide wire 44 can include a cutting tip configured to cut through the first and second bone locations 31a and 31b, alone or in combination with the sacrum S as desired.

Once the guide wire 44 is in place, a drill can be guided along the guide wire so as to create the bore holes in the first and second bone locations 31a and 31b, alone or in combination with the sacrum S as desired. The bore holes may be drilled with the same drill bit in a single drilling step, for instance if the maximum outer cross-sectional dimensions of the first and second shafts are substantially the same, or in separate drilling steps, which can be with different drill bits if the maximum cross-sectional dimensions of the first and second shafts are different than each other. The above steps can be repeated to produce as many bore holes in the first and second bone locations 31a and 31b as desired. The drill bit is removed leaving the bone prepared for insertion of one or more of the bone fixation implants 32. Alternatively still, as described above, either or both of the first and second implant segments 36 and 38 can be self-drilling.

The sacral fracture can be reduced prior to insertion of the one or more of the bone fixation implants 32, particularly when none of the bone fixation implants 32 are configured to achieve compression of the first and second ilium bones 33a and 33b toward each other. Alternatively or additionally, at least one of the bone fixation implants 32 can be configured to achieve compression of the first and second ilium bones 33a and 33b toward each other, as described above.

Alternatively, the guide wire 144 can be introduced through the channel 207 and through the first bone location 35a. Further, the guide wire 144 can be introduced through the channel 156, for instance, if the implant segment 136 has been previously threadedly driven into the first bone location 35a. Alternatively, the guide wire 144 can be threadedly driven into the second bone location 35b prior to guiding the implant segment 136 along the guide wire 144 to the first bone location 35a.

The foregoing description is provided for the purpose of explanation and is not to be construed as limiting the invention. While various embodiments have been described with reference to preferred embodiments or preferred methods, it is understood that the words which have been used herein are words of description and illustration, rather than words of limitation. Furthermore, although the embodiments have been described herein with reference to particular structure, methods, and embodiments, the invention is not intended to be limited to the particulars disclosed herein. For instance, it should be appreciated that structure and methods described in association with one embodiment are equally applicable to all other embodiments described herein unless otherwise indicated. Those skilled in the relevant art, having the benefit of the teachings of this specification, may effect numerous modifications to the invention as described herein, and changes may be made without departing from the spirit and scope of the invention, for instance as set forth by the appended claims.

The invention claimed is:

1. A sacral fixation implant, comprising:
   an implant segment including a shaft, the implant segment defining a proximal end and a distal end spaced from the proximal end in a distal direction, the implant segment further defining a channel that extends through the shaft from the proximal end to the distal end, the channel defining an inner diameter, wherein the implant segment is configured to be inserted through an ilium bone in the distal direction, and the implant segment includes an abutment surface that is both monolithic with the shaft and configured to abut the ilium bone so as to prevent further insertion of the shaft through the ilium bone;

a guide wire configured to be received in the channel such that the guide wire extends through the implant segment from the proximal end to the distal end, such that the guide wire extends out the distal end, the guide wire including at least one external thread configured to be driven at least into a sacrum that is spaced from the ilium bone, the at least one external thread defining an outer diameter that is greater than the inner diameter, wherein the guide wire is a Kirschner wire; and a locking member configured to fix the implant segment to the guide wire with respect to: 1) movement along the guide wire at least in a proximal direction opposite the distal direction, and 2) rotation about the guide wire.

2. The sacral fixation implant as recited in claim 1, wherein the locking member comprises a locking cap having a flexible wall that is configured to compress against the guide wire in response to a compression force applied to the flexible wall, thereby securing the shaft to the guide wire with respect to movement along the guide wire in the distal direction.

3. The sacral fixation implant as recited in claim 2, wherein the locking cap is sized to be at least partially received in an aperture that extends through the proximal end, such that an inner surface that defines the aperture is configured to apply the compression force to the flexible wall as the locking cap is inserted into the aperture.

4. The sacral fixation implant as recited in claim 3, wherein an outer surface of the flexible wall and the inner surface define threads that are configured to mate with each other when the locking cap is inserted into the aperture.

5. The sacral fixation implant as recited in claim 4, wherein the locking cap comprises at least one compression slot that extends through the flexible wall.

6. The sacral fixation implant as recited in claim 3, wherein the channel further defines the aperture.

7. The sacral fixation implant as recited in claim 1, wherein the guide wire is threaded, and at least one of the first and second locking members comprises a locking nut that is internally threaded and threadable onto the guide wire so as to abut the shaft and apply a force against the shaft that urges the shaft to translate along the guide wire in the distal direction.

8. The sacral fixation implant as recited in claim 1, wherein distal end is serrated so as to define a cutting surface configured to drill a bore hole through the first ilium bone.

9. The sacral fixation implant as recited in claim 1, wherein the shaft defines at least one external thread at least at a location adjacent the proximal end, the at least one external thread configured to be driven at least into the ilium bone.

10. The sacral fixation implant as recited in claim 9, wherein the guide wire is configured to be driven at least into the sacrum while the guide wire extends through the implant segment.

11. The sacral fixation implant as recited in claim 10, wherein the at least one external thread of each of the shaft and the guide wire is at least one of self tapping and self drilling.

12. The sacral fixation implant as recited in claim 10, wherein the at least one external thread of the shaft has a first maximum outer diameter, and the at least one thread of the guide wire has a second maximum outer diameter that is less than the first maximum outer diameter.

13. The sacral fixation implant as recited in claim 10, wherein the at least one external thread of the shaft has a first pitch, and the at least one external thread of the guide wire has a second pitch that is greater than the first pitch.

14. The sacral fixation implant as recited in claim 1, wherein the locking member is further configured to rotatably couple the implant segment to the guide wire.

15. The sacral fixation implant as recited in claim 1, wherein the implant segment is a first implant segment, the shaft is a first shaft, the proximal end is a first proximal end, the distal end is a first distal end the ilium bone is a first ilium bone, the abutment surface is a first abutment surface, the channel is a first channel, and the locking member is a first locking member, the sacral fixation implant further comprising:

a second implant segment having a second shaft sized to be inserted through a second ilium bone, the second implant segment defining a second proximal end and a second distal end opposite the second proximal end, and a second abutment surface that extends out from the second shaft and is configured to abut the second ilium bone so as to prevent further insertion of the second shaft through the second ilium bone, wherein at least the second distal end is sized to be received in the first channel at a location between the first and second ilium bones.

16. The sacral fixation implant as recited in claim 15, wherein the second implant segment defines a second channel that extends from the second proximal end to the second distal end, and the second channel is sized to receive the guide wire as the second shaft is inserted through the second ilium bone.

17. The sacral fixation implant as recited in claim 16, further comprising a second locking member configured to secure the second shaft to the guide wire with respect to movement of the second shaft at least in a second proximal direction from the second distal end toward the second proximal end.

18. The sacral fixation implant as recited in claim 17, wherein the second locking member is further configured to secure the second shaft to the guide wire with respect to movement along the guide wire in a second distal direction opposite the second proximal direction.

19. The sacral fixation implant as recited in claim 15, wherein the guide wire is threaded, and at least one of the first and second locking members comprises a locking nut that is internally threaded and threadable onto the guide wire so as to abut the shaft and apply a force against the shaft that urges the shaft to translate along the guide wire in the second distal direction.

20. The sacral fixation implant as recited in claim 15, wherein the second distal end is serrated so as to define a cutting surface configured to drill a bore hole through the second ilium bone.

* * * * *